(12) United States Patent
Henderson et al.

(10) Patent No.: US 10,154,829 B2
(45) Date of Patent: Dec. 18, 2018

(54) MODULAR ULTRASOUND SYSTEM

(71) Applicant: EDAN INSTRUMENTS, INC., Shenzhen (CN)

(72) Inventors: Richard Henderson, Sunnyvale, CA (US); Sean Murphy, Sunnyvale, CA (US)

(73) Assignee: EDAN INSTRUMENTS, INC., Shenzhen (CN)

( * ) Notice: Subject to any disclaimer, the term of this patent is extended or adjusted under 35 U.S.C. 154(b) by 0 days.

(21) Appl. No.: 15/439,690

(22) Filed: Feb. 22, 2017

(65) Prior Publication Data

US 2017/0238901 A1    Aug. 24, 2017

Related U.S. Application Data

(60) Provisional application No. 62/298,910, filed on Feb. 23, 2016.

(51) Int. Cl.
| A61B 8/00 | (2006.01) |
| G06F 1/16 | (2006.01) |
| G06F 3/01 | (2006.01) |
| A61B 6/00 | (2006.01) |

(52) U.S. Cl.
CPC .......... *A61B 8/4427* (2013.01); *A61B 6/4405* (2013.01); *A61B 6/4411* (2013.01); *A61B 6/462* (2013.01); *A61B 6/464* (2013.01); *A61B 6/467* (2013.01); *A61B 8/462* (2013.01); *G06F 1/162* (2013.01); *G06F 3/013* (2013.01); *G06F 3/017* (2013.01)

(58) Field of Classification Search
CPC ..... A61B 8/4427; A61B 8/462; A61B 6/4405; A61B 6/4411; A61B 6/462; A61B 6/464; A61B 6/467; G06F 3/017; G06F 1/162; G06F 3/013
See application file for complete search history.

(56) References Cited

U.S. PATENT DOCUMENTS

| 5,596,261 | A | 1/1997 | Suyama |
| 6,067,224 | A | 5/2000 | Nobuchi |
| 6,471,651 | B1 | 10/2002 | Hwang et al. |
| 6,491,630 | B1 | 12/2002 | Saccardo et al. |
| 7,352,570 | B2 | 4/2008 | Smith et al. |
| 8,482,259 | B2 | 7/2013 | Mueller |
| 9,074,736 | B2 | 7/2015 | Recker et al. |

(Continued)

FOREIGN PATENT DOCUMENTS

| CN | 105877781 | 8/2016 |
| WO | WO 2006/111874 A2 | 10/2006 |

OTHER PUBLICATIONS

U.S. Appl. No. 15/494,249, filed Apr. 21, 2017, Henderson et al.

(Continued)

*Primary Examiner* — Ariel Balaoing
(74) *Attorney, Agent, or Firm* — Gilberto M. Villacorta; Brett P. Belden; Foley & Lardner LLP

(57) ABSTRACT

An ultrasound system includes a display, an actuator, a user interface, and a processing circuit. The actuator is configured to control at least one of a position or an orientation of the display. The user interface is configured to receive a user input. The processing circuit is configured to cause the actuator to adjust the at least one of the position or orientation of the display based on the user input.

15 Claims, 34 Drawing Sheets

(56) References Cited

U.S. PATENT DOCUMENTS

| | | | |
|---|---|---|---|
| 9,629,606 B2 | 4/2017 | Henderson et al. | |
| 2003/0090473 A1 | 5/2003 | Joshi | |
| 2004/0145321 A1* | 7/2004 | Yasui | F16H 59/68 318/135 |
| 2004/0215408 A1 | 10/2004 | Lamer et al. | |
| 2005/0251035 A1 | 11/2005 | Wong et al. | |
| 2006/0063595 A1* | 3/2006 | Kondo | A63F 13/02 463/46 |
| 2008/0055826 A1 | 3/2008 | Smith et al. | |
| 2008/0089587 A1* | 4/2008 | Kim | G06F 3/017 382/190 |
| 2008/0119731 A1 | 5/2008 | Becerra et al. | |
| 2008/0146922 A1 | 6/2008 | Steins et al. | |
| 2009/0043203 A1 | 2/2009 | Pelissier et al. | |
| 2010/0262012 A1 | 10/2010 | Wu | |
| 2011/0193818 A1* | 8/2011 | Chen | G06F 3/041 345/174 |
| 2013/0197364 A1* | 8/2013 | Han | A61B 8/4405 600/440 |
| 2013/0234931 A1* | 9/2013 | Keranen | G06F 3/017 345/156 |
| 2014/0098049 A1 | 4/2014 | Koch et al. | |
| 2014/0121524 A1 | 5/2014 | Chiang et al. | |
| 2016/0007965 A1 | 1/2016 | Murphy et al. | |
| 2016/0048365 A1 | 2/2016 | Henderson et al. | |
| 2016/0049066 A1 | 2/2016 | Henderson et al. | |

OTHER PUBLICATIONS

International Search Report and Written Opinion issued in related International Patent Application No. PCT/US2015/045088, dated Jul. 14, 2016.

International Preliminary Report on Patentability issued in related International Patent Application No. PCT/US2015/045088, dated Feb. 23, 2017.

Notice of Allowance issued in related U.S. Appl. No. 14/825,984, dated Dec. 9, 2016.

International Preliminary Report on Patentability issued in related International Patent Application No. PCT/US2015/039610, dated Jan. 10, 2017.

International Search Report and Written Opinion issued in related International Patent Application No. PCT/US2015/039610, dated Mar. 25, 2016.

* cited by examiner

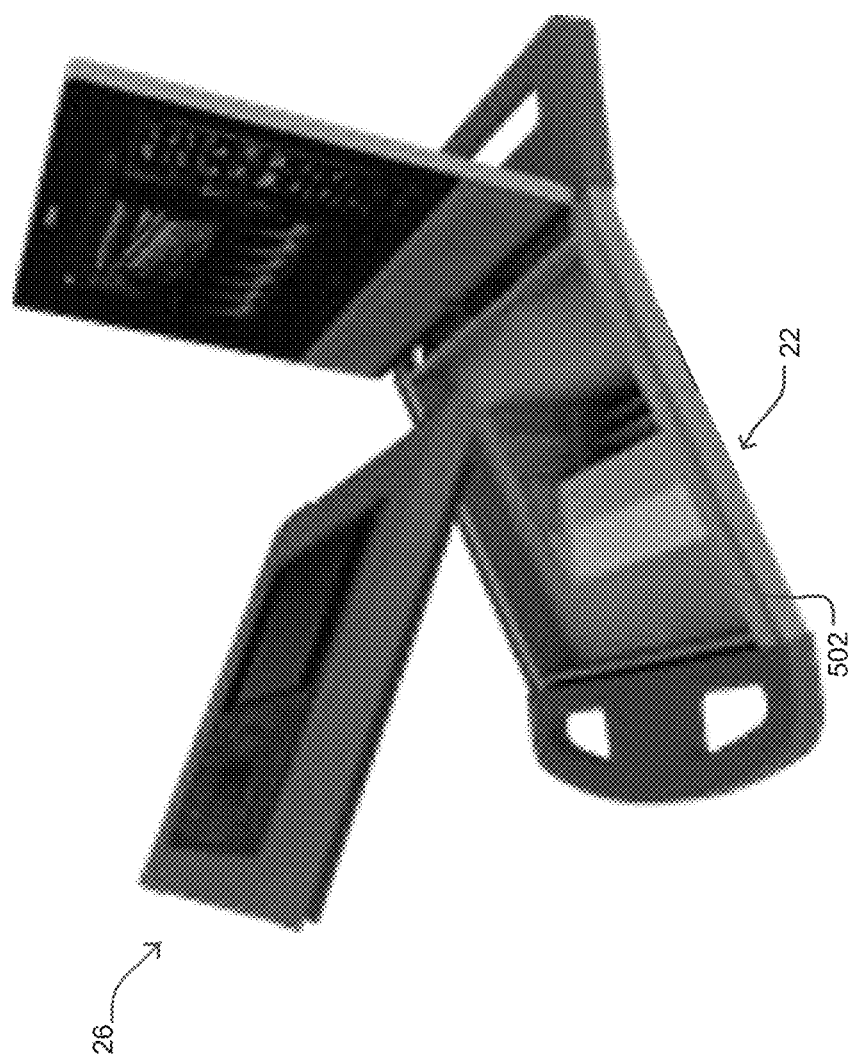

MODULAR ULTRASOUND SYSTEM

CROSS-REFERENCE TO RELATED APPLICATIONS

The present application claims the benefit of and priority to U.S. Provisional Application No. 62/298,910, titled "Modular Ultrasound System," filed Feb. 23, 2016, the disclosure of which is incorporated herein in its entirety for all purposes.

TECHNICAL FIELD

The present disclosure generally relates to ultrasound systems. In some implementations, the present disclosure relates to cart-based ultrasound systems with various features relating to form factor, modularity, user interface, and display manipulation.

BACKGROUND

In diagnostic ultrasound, cart-based systems can be used to position an ultrasound system adjacent to a patient for performing an ultrasound procedure on the patient. A transducer probe assembly can be used to acquire diagnostic information regarding the patient and transmit the diagnostic information to the ultrasound system. The ultrasound system can analyze and/or display the diagnostic information.

SUMMARY

One embodiment relates to an ultrasound system. The ultrasound system includes a display, an actuator, a user interface, and a processing circuit. The actuator is configured to control at least one of a position or an orientation of the display. The user interface is configured to receive a user input. The processing circuit is configured to cause the actuator to adjust the at least one of the position or orientation of the display based on the user input.

Another embodiment relates to an ultrasound system. The ultrasound system includes a platform including a housing, a display attached to the housing, a drive system, and a display control circuit. The drive system is configured to adjust at least one of a position or an orientation of the display. The display control circuit is configured to control operation of the drive system based on an indication of a user input.

Another embodiment relates to a method. The method includes receiving, at a user interface, a user input indicating a command to control at least one of a position or an orientation of an ultrasound display. The method includes extracting the command from the user input, by a processing circuit, the command including at least one of a traverse command configured to traverse the ultrasound display along a first axis, a tilt command configured to tilt the ultrasound display about a second axis, or a swivel command configured to swivel the ultrasound display about a third axis. The method includes controlling, by an actuator, the at least one of the position or orientation of the ultrasound display based on the command.

BRIEF DESCRIPTION OF THE DRAWINGS

FIGS. 22A-22B illustrate perspective views of a portable ultrasound system with an ultrasound electronics module to be received in the portable ultrasound system according to an illustrative embodiment.

DETAILED DESCRIPTION

Figure 1:
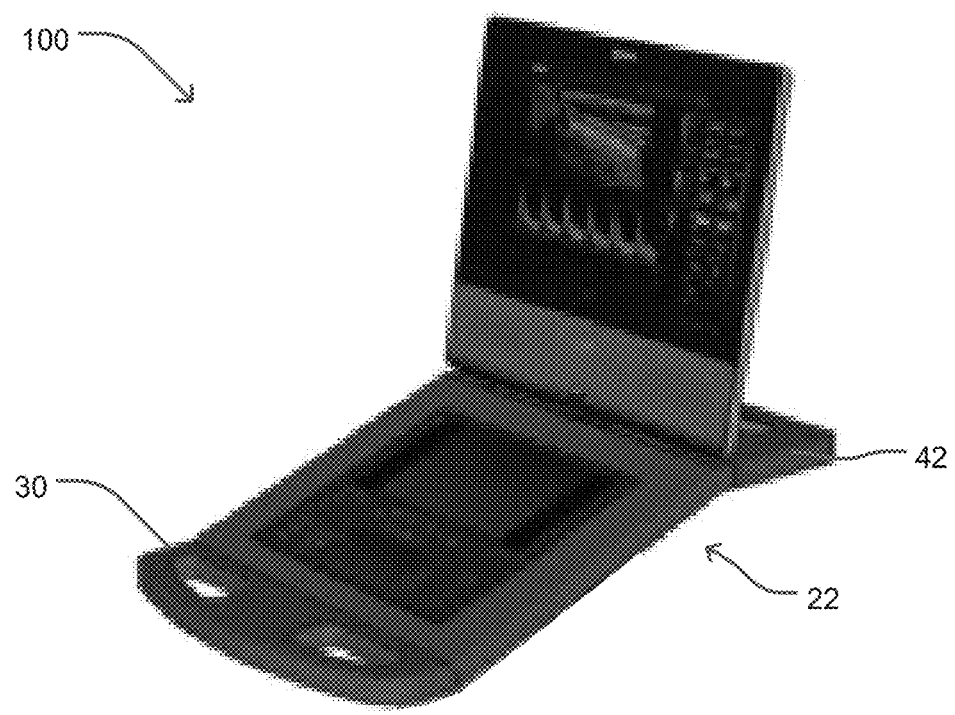
FIG. 1 illustrates a perspective view of a portable ultrasound system according to an illustrative embodiment.

Before turning to the figures which illustrate the exemplary embodiments in detail, it should be understood that the application may be not limited to the details or methodology set forth in the description or illustrated in the figures. It should also be understood that the terminology may be for the purpose of description only, and should not be regarded as limiting.

Referring to the figures generally, ultrasound devices, systems, and methods are disclosed with advantageous form factor, modularity, user interface, and/or display manipulation features. An ultrasound system, such as a portable ultrasound cart system, can include a platform, an ultrasound system positioned on the platform, hookups/connectors and/or mounting/holding structures for ultrasound devices and tools (e.g., transducers/probes, gels, bottles, wipes, etc.), handles, power supplies (e.g., batteries, backup batteries). The ultrasound system can include an ultrasound electronics module, a display, and additional components and electronics (e.g., power supply, processors, memories, etc.). The ultrasound electronics module can be modular and/or removable, such that the ultrasound cart system can be customized, upgraded, or otherwise modified to suit specific user requirements. The ultrasound electronics module can include one or more user interfaces. The display can be attached to the platform and, in some embodiments, can include sensor(s) positioned along a perimeter of the display. The platform can include a housing. The housing can include actuation components located inside the housing and configured to control/articulate the position and orientation of the display, such as for shifting the display along a first axis (e.g., traverse axis passing from a first side to a second side of the platform), rotating the display about a second axis (e.g., swivel axis substantially perpendicular to a plane of the platform), and/or rotating the display about a third axis (e.g., tilt axis parallel to or collinear with the first axis). In some embodiments, the position and orientation of the display can be controlled electronically by controlling the actuation components based on user input received at the one or more user interfaces of the ultrasound electronics module (e.g., user input indicating at least one of a traverse command, a swivel command, or a tilt command). In some embodiments, the position and orientation of the display can additionally or alternatively be controlled manually based on user input received at the sensor(s) positioned along the perimeter of the display and forces applied to the display.

Embodiments of ultrasound systems as disclosed herein can provide, among other features, advantageous form factor, modularity, user interface, and display manipulation features, such as by allowing the display to be directly attached to the platform and controlled electronically, manually, or both electronically and manually, locating the actuation components for controlling/articulating the display position and orientation inside the housing, using a modular ultrasound electronics module that can be replaced by a user, etc.

Referring now to FIG. 1, portable ultrasound system 100 is shown in accordance with some embodiments. Portable ultrasound system 100 can include platform 22, ultrasound electronics module 26 received in platform 22, display 20 attached to platform 22, and handles 30 attached to platform 22 adjacent to where ultrasound electronics module 26 is received in platform 22. Handle(s) 42 may be positioned on an opposite side of platform 30 from handles 30.

Figure 2:
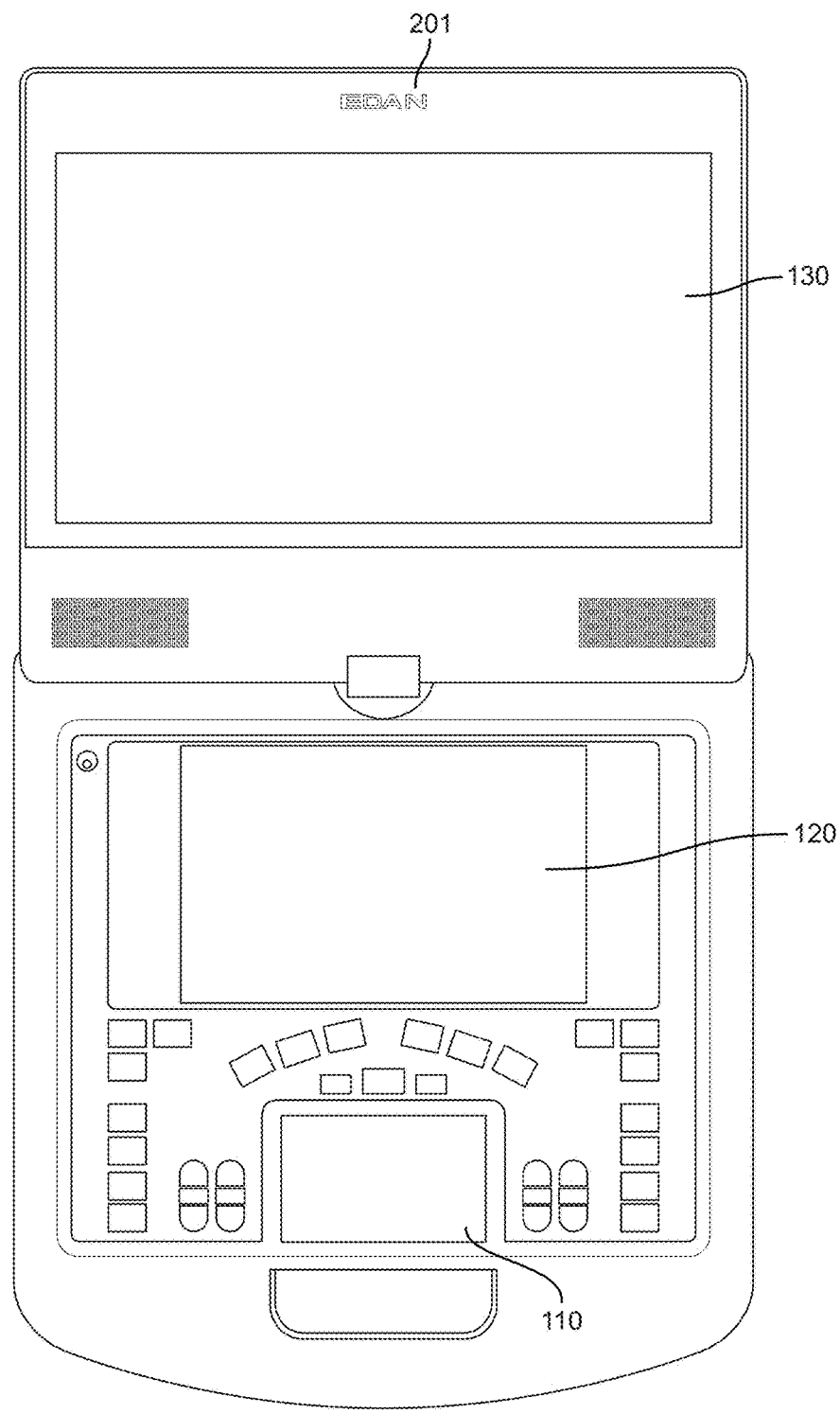
FIG. 2 illustrates a front view of a display and ultrasound electronics module of a portable ultrasound system according to an illustrative embodiment.

Referring now to FIG. 2, display 20 and ultrasound electronics module 26 are shown in accordance with some embodiments. Display 20 can include a display screen (e.g., main screen 130) and hardware logo 201. Ultrasound electronics module 26 can include one or more user interfaces, such as touchscreens 110, 120. Main screen 130 and touchscreens 110, 120 can display information, such as diagnostic information related to an ultrasound procedure. Touchscreens 110, 120 can receive user input, such as touch input from a user's fingers, from a touch device (e.g., stylus, pen), etc. Hardware logo 201 can illuminate. Hardware logo 201 may be a transparent or semi-transparent material backed by a light source such as a light emitting diode. In some embodiments, hardware logo 201 is located on a face of display 20 oriented towards a user. In other embodiments, hardware logo 201 may be located on other faces of display 20 such as the back, side, etc. In some embodiments, main screen 130 may be a touchscreen or include one or more touch-sensitive or otherwise selectable portions. In some embodiments, main screen 130 may include one or more sensors, such as proximity sensors.

Figure 3:
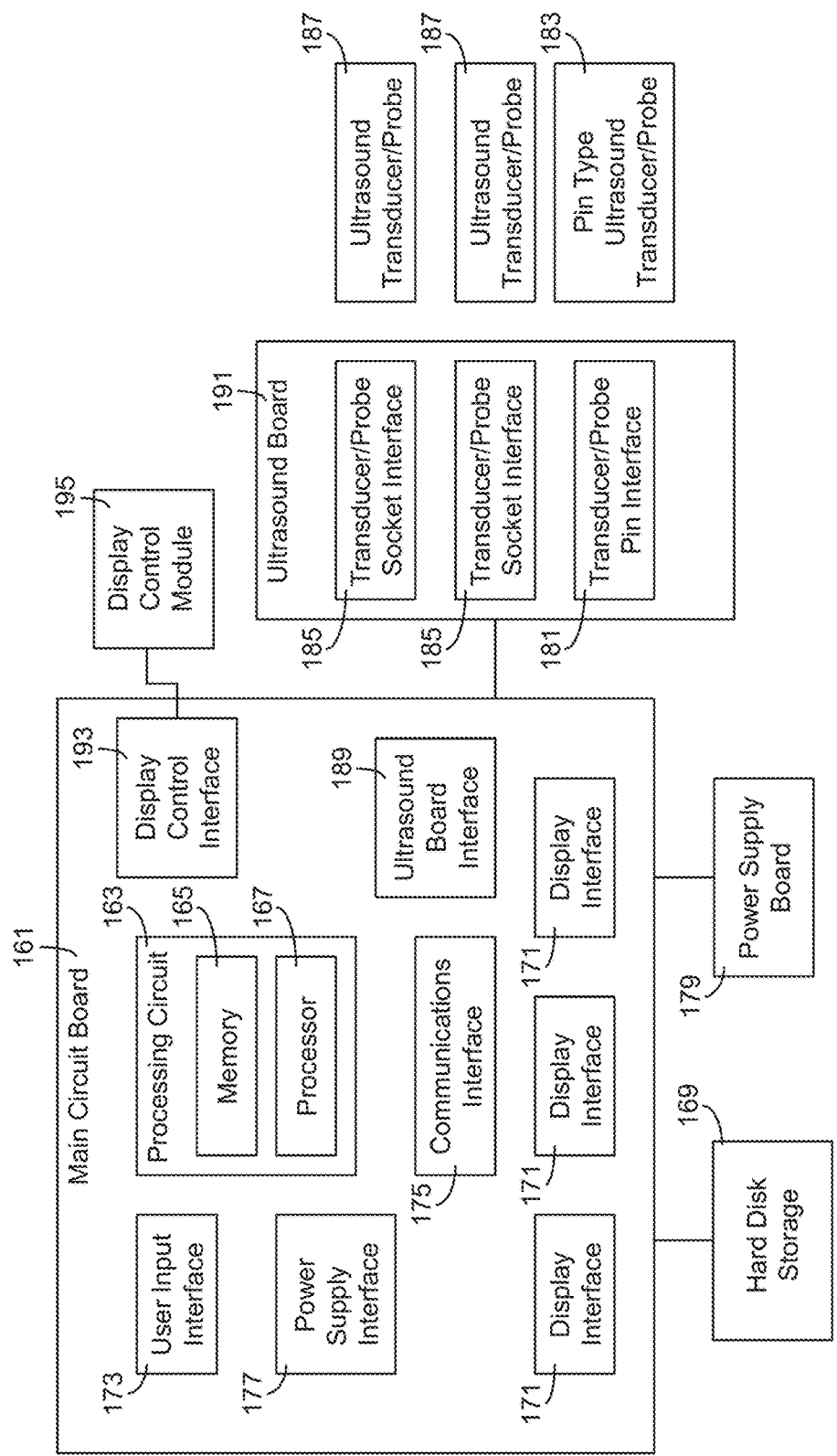
FIG. 3 illustrates a block diagram of various electronic components of a portable ultrasound system according to an illustrative embodiment.

Referring now to FIG. 3, a block diagram shows internal components of some embodiments of portable ultrasound system 100. Portable ultrasound system 100 includes main circuit board 161. Main circuit board 161 carries out computing tasks to support the functions of portable ultrasound system 100 and provides connection and communication between various components of portable ultrasound system 100. In some embodiments, main circuit board 161 is configured so as to be a replaceable and/or upgradeable module.

To perform computational, control, and/or communication tasks, main circuit board 161 includes processing circuit 163. Processing circuit 163 is configured to perform general processing and to perform processing and computational tasks associated with specific functions of portable ultrasound system 100. For example, processing circuit 163 may perform calculations and/or operations related to producing an image from signals and or data provided by ultrasound equipment, running an operating system for portable ultrasound system 100, receiving user inputs, etc. Processing circuit 163 may include memory 165 and processor 167 for use in processing tasks. For example, processing circuit may perform calculations and/or operations.

Processor 167 may be, or may include, one or more microprocessors, application specific integrated circuits (ASICs), circuits containing one or more processing components, a group of distributed processing components, circuitry for supporting a microprocessor, or other hardware configured for processing. Processor 167 is configured to execute computer code. The computer code may be stored in memory 165 to complete and facilitate the activities described herein with respect to portable ultrasound system 100. In other embodiments, the computer code may be retrieved and provided to processor 167 from hard disk storage 169 or communications interface 175 (e.g., the computer code may be provided from a source external to main circuit board 161).

Memory 165 can be any volatile or non-volatile computer-readable storage medium capable of storing data or computer code relating to the activities described herein. For example, memory 165 may include modules which are computer code modules (e.g., executable code, object code, source code, script code, machine code, etc.) configured for execution by processor 167. Memory 165 may include computer executable code related to functions including ultrasound imaging, battery management, handling user inputs, displaying data, transmitting and receiving data using a wireless communication device, etc. In some embodiments, processing circuit 163 may represent a collection of multiple processing devices (e.g., multiple processors, etc.). In such cases, processor 167 represents the collective processors of the devices and memory 165 represents the collective storage devices of the devices. When executed by processor 167, processing circuit 163 is configured to complete the activities described herein as associated with portable ultrasound system 100. As referenced herein, a computer-readable storage medium is non-transitory (i.e., does not include solely signals in space).

Hard disk storage 169 may be a part of memory 165 and/or used for non-volatile long term storage in portable ultrasound system 100. Hard disk storage 169 may store local files, temporary files, ultrasound images, patient data, an operating system, executable code, and any other data for supporting the activities of portable ultrasound device 100 described herein. In some embodiments, hard disk storage is embedded on main circuit board 161. In other embodiments, hard disk storage 169 is located remote from main circuit board 161 and coupled thereto to allow for the transfer of data, electrical power, and/or control signals. Hard disk 169 may be an optical drive, magnetic drive, a solid state hard drive, flash memory, etc.

In some embodiments, main circuit board 161 includes communications interface 175. Communications interface 175 may include connections that enable communication between components of main circuit board 161 and communications hardware. For example, communications interface 175 may provide a connection between main circuit board 161 and a network device (e.g., a network card, a wireless transmitter/receiver, etc.). In further embodiments, communications interface 175 may include additional circuitry to support the functionality of attached communications hardware or to facilitate the transfer of data between communications hardware and main circuit board 161. In other embodiments, communications interface 175 may be a system on a chip (SOC) or other integrated system which allows for transmission of data and reception of data. In such a case, communications interface 175 may be coupled directly to main circuit board 161 as either a removable package or embedded package.

Some embodiments of portable ultrasound system 100 include power supply board 179. Power supply board 179 includes components and circuitry for delivering power to components and devices within and/or attached to portable ultrasound system 100. In some embodiments, power supply board 179 includes components for alternating current and direct current conversion, for transforming voltage, for delivering a steady power supply, etc. These components may include transformers, capacitors, modulators, etc. to perform the above functions. In further embodiments, power supply board 179 includes circuitry for determining the available power of a battery power source. In other embodiments, power supply board 179 includes circuitry for switching between power sources. For example, power supply board 179 may draw power from a backup battery while a main battery is switched. In further embodiments, power supply board 179 includes circuitry to operate as an uninterruptable power supply in conjunction with a backup battery. Power supply board 179 also includes a connection to main circuit board 161. This connection may allow power supply board 179 to send and receive information from main circuit board 161. For example, power supply board 179 may send information to main circuit board 161 allowing for the determination of remaining battery power. The connection to main circuit board 161 may also allow main circuit board 161 to send commands to power supply board 179. For example, main circuit board 161 may send a command to power supply board 179 to switch from source of power to another (e.g., to switch to a backup battery while a main battery is switched). In some embodiments, power supply board 179 is configured to be a module. In such cases, power supply board 179 may be configured so as to be a replaceable and/or upgradeable module.

Main circuit board 161 may also include power supply interface 177 which facilitates the above described communication between power supply board 179 and main circuit board 161. Power supply interface 177 may include connections which enable communication between components of main circuit board 161 and power supply board 179. In further embodiments, power supply interface 177 includes additional circuitry to support the functionality of power supply board 179. For example, power supply interface 177 may include circuitry to facilitate the calculation of remaining battery power, manage switching between available power sources, etc. In other embodiments, the above described functions of power supply board 179 may be carried out by power supply interface 177. For example, power supply interface 177 may be a SOC or other integrated system. In such a case, power supply interface 177 may be coupled directly to main circuit board 161 as either a removable package or embedded package. Power supply interface 177 may be configured to facilitate communication between power supply board 179 and other components, such as ultrasound board 191.

Figure 28:
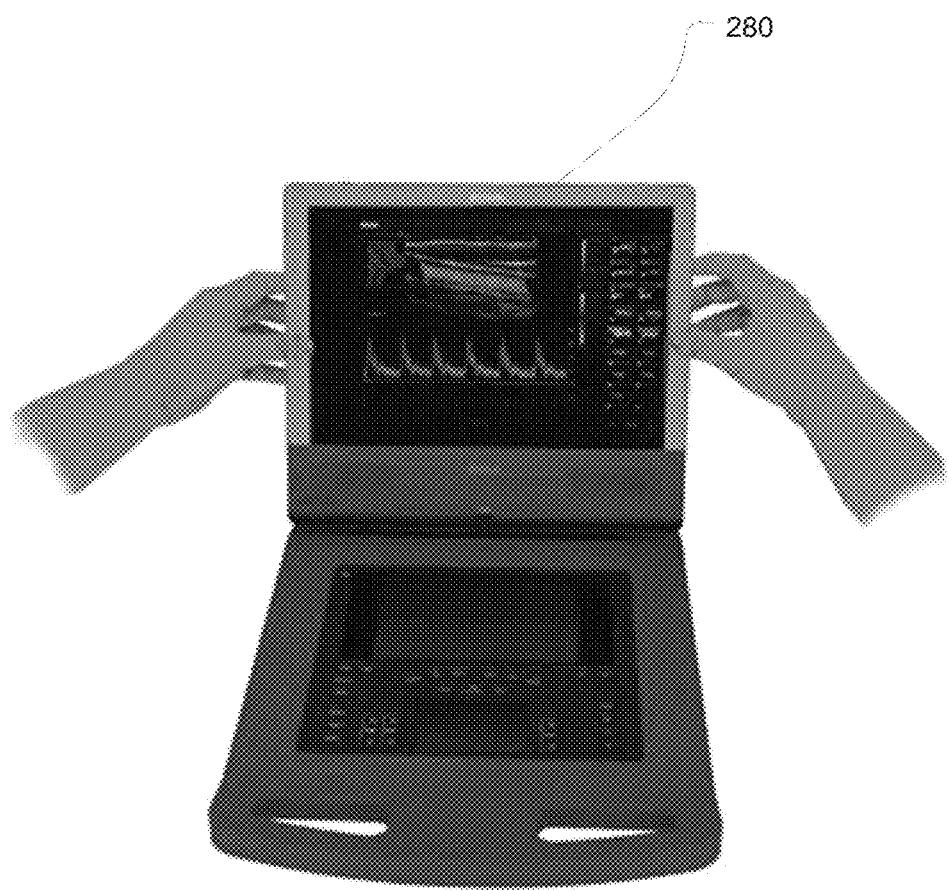
FIG. 28 illustrates a perspective view of sensors of a display of a portable ultrasound system according to an illustrative embodiment.

With continued reference to FIG. 3, some embodiments of main circuit board 161 include user input interface 173. User input interface 173 may include connections which enable communication between components of main circuit board 161 and user input device hardware. For example, user input interface 173 may provide a connection between main circuit board 161 and a capacitive touchscreen, resistive touchscreen, mouse, keyboard, buttons, and/or a controller for the preceding. In one embodiment, user input interface 173 couples controllers for touchscreen 110, touchscreen 120, and main screen 130 to main circuit board 161. In other embodiments, user input interface 173 includes controller circuitry for touchscreen 110, touchscreen 120, and main screen 130. In some embodiments, main circuit board 161 includes a plurality of user input interfaces 173. For example, each user input interface 173 may be associated with a single input device (e.g., touchscreen 110, touchscreen 120, a keyboard, buttons, etc.). In some embodiments, one or more user input interfaces 173 may be associated with sensors of display 20 (e.g., sensors 280 positioned along a perimeter of display 20 for receiving user inputs for controlling the position and orientation of display 20 as shown in FIG. 28, etc.).

In further embodiments, user input interface 173 may include additional circuitry to support the functionality of attached user input hardware or to facilitate the transfer of data between user input hardware and main circuit board 161. For example, user input interface 173 may include controller circuitry so as to function as a touchscreen controller. User input interface 173 may also include circuitry for controlling haptic feedback devices associated with user input hardware. In other embodiments, user input interface 173 may be a SOC or other integrated system which allows for receiving user inputs or otherwise controlling user input hardware. In such a case, user input interface 173 may be coupled directly to main circuit board 161 as either a removable package or embedded package.

In some embodiments, ultrasound electronics module 26 includes ultrasound board 191. Main circuit board 161 may include ultrasound board interface 189 which facilitates communication between ultrasound board 191 and main circuit board 161. Ultrasound board interface 189 may include connections which enable communication between components of main circuit board 161 and ultrasound board 191. In further embodiments, ultrasound board interface 189 includes additional circuitry to support the functionality of ultrasound board 191. For example, ultrasound board interface 189 may include circuitry to facilitate the calculation of parameters used in generating an image from ultrasound data provided by ultrasound board 191. In some embodiments, ultrasound board interface 189 is a SOC or other integrated system. In such a case, ultrasound board interface 189 may be coupled directly to main circuit board 161 as either a removable package or embedded package. Ultrasound board interface 189 includes connections which facilitate use of a modular ultrasound board 191. Ultrasound board 191 may be a module (e.g., ultrasound module) capable of performing functions related to ultrasound imaging (e.g., multiplexing sensor signals from an ultrasound probe/transducer, controlling the frequency of ultrasonic waves produced by an ultrasound probe/transducer, etc.). The connections of ultrasound board interface 189 may facilitate replacement of ultrasound board 191 (e.g., to replace ultrasound board 191 with an upgraded board or a board for a different application). For example, ultrasound board interface 189 may include connections which assist in accurately aligning ultrasound board 191 and/or reducing the likelihood of damage to ultrasound board 191 during removal and or attachment (e.g., by reducing the force required to connect and/or remove the board, by assisting, with a mechanical advantage, the connection and/or removal of the board, etc.).

In embodiments of portable ultrasound system 100 including ultrasound board 191, ultrasound board 191 includes components and circuitry for supporting ultrasound imaging functions of portable ultrasound system 100. In some embodiments, ultrasound board 191 includes integrated circuits, processors, and memory. Ultrasound board 191 may also include one or more transducer/probe socket interfaces 185. Transducer/probe socket interface 185 enables ultrasound transducer/probe 187 (e.g., a probe with a socket type connector) to interface with ultrasound board 191. For example, transducer/probe socket interface 185 may include circuitry and/or hardware connecting ultrasound transducer/probe 187 to ultrasound board 191 for the transfer of electrical power and/or data. Transducer/probe socket interface 185 may include hardware which locks ultrasound transducer/probe 187 into place (e.g., a slot which accepts a pin on ultrasound transducer/probe 187 when ultrasound transducer/probe 187 is rotated). In some embodiments, ultrasound board 191 includes two transducer/probe socket interfaces 185 to allow the connection of two socket type ultrasound transducers/probes 187.

In some embodiments, ultrasound board 191 also includes one or more transducer/probe pin interfaces 181. Transducer/probe pin interface 181 enables ultrasound transducer/probe 183 (e.g., a probe with a pin type connector) to interface with ultrasound board 191. Transducer/probe pin interface 181 may include circuitry and/or hardware connecting ultrasound transducer/probe 183 to ultrasound board 191 for the transfer of electrical power and/or data. Transducer/probe pin interface 181 may include hardware which locks ultrasound transducer/probe 183 into place. In some embodiments, ultrasound transducer/probe 183 is locked into place with a locking lever system. In some embodiments, ultrasound board 191 includes more than one transducer/probe pin interfaces 181 to allow the connection of two or more pin type ultrasound transducers/probes 183. In such cases, portable ultrasound system 100 may include one or more locking lever systems. In further embodiments, ultrasound board 191 may include interfaces for additional types of transducer/probe connections.

With continued reference to FIG. 3, some embodiments of main circuit board 161 include display interface 171. Display interface 171 may include connections which enable communication between components of main circuit board 161 and display device hardware. For example, display interface 171 may provide a connection between main circuit board 161 and a liquid crystal display, a plasma display, a cathode ray tube display, a light emitting diode display, an organic light emitting diode display, and/or a display controller or graphics processing unit for the proceeding or other types of display hardware. In some embodiments, the connection of display hardware to main circuit board 161 by display interface 171 allows a processor or dedicated graphics processing unit on main circuit board 161 to control and/or send data to display hardware. Display interface 171 may be configured to send display data to display device hardware in order to produce an image. In some embodiments, main circuit board 161 includes multiple display interfaces 171 for multiple display devices (e.g., three display interfaces 171 connect three displays to main circuit board 161). In other embodiments, one display interface 171 may connect and/or support multiple displays. In one embodiment, three display interfaces 171 couple touchscreen 110, touchscreen 120, and main screen 130 to main circuit board 161.

In further embodiments, display interface 171 may include additional circuitry to support the functionality of attached display hardware or to facilitate the transfer of data between display hardware and main circuit board 161. For example, display interface 171 may include controller circuitry, a graphics processing unit, video display controller, etc. In some embodiments, display interface 171 may be a SOC or other integrated system which allows for displaying images with display hardware or otherwise controlling display hardware. Display interface 171 may be coupled directly to main circuit board 161 as either a removable package or embedded package. Processing circuit 163 in conjunction with one or more display interfaces 171 may display images on one or more of touchscreen 110, touchscreen 120, and main screen 130.

Generally, display circuitry may provide for the display of an image on a display screen. The image may result from user input (e.g., a pointer displayed as moving across a display in response to user input on a touch device or through a computer mouse). The image may also be one that is displayed upon the occurrence of certain triggering events, inputs, and/or objects. In some embodiments of the disclosure, an image is displayed using multiple displays of a multi-display device.

Referring still to FIG. 3, some embodiments of the disclosure include displaying images on a portable ultrasound system 100. In other embodiments, images may be displayed on or with other devices (e.g., portable computing devices, personal computing devices, etc.). In some embodiments, main circuit board 161 and/or one or more display interfaces 171 control one or more displays. The displays are controlled to produce one or more images on one or more displays. Processing circuit 163 may determine what images and the characteristics of those images to display. Processing circuit 163 may further determine on which display to display the images in the case of a multi-display device. In some embodiments, these determinations are made based on user inputs. In other embodiments, the determinations are made in response to triggering events, inputs, and/or objects. Processing circuit 163 may make these determinations by executing, using processor 167, instructions or computer code stored in memory 165, stored in hard disk storage 169, and/or acquired using communications interface 175. In some embodiments, processing circuit 163 retrieves, from memory 165 and/or hard disk storage 169, display instructions for an image to be displayed in response to executed code and/or instructions. Processing circuit 163 may then send control instructions to one or more display interfaces 171 which display an image according to those instructions on one or more displays. In some embodiments, main circuit board 161 and/or display interface 171 may include a graphics processing unit which performs or assists in preforming these functions.

For some events, instructions for displaying a certain corresponding image or series of images may be stored in memory 165 and/or hard disk storage 169. The occurrence of an event may trigger an instance in which processor 167 retrieves the instructions and executes them. One such event may be receiving user input, such as receiving user input at touchscreens 110, 120, or at sensors 280. By executing the instructions for displaying an image corresponding to an event, processing circuit 163, one or more display interfaces 171, and/or display hardware cause an image or series of images to be displayed to a user.

In some embodiments, main circuit board 161 includes display control interface 193. Display control interface 193 can be similar to other components of main circuit board 161, such as ultrasound board interface 189. Display control interface is configured to communicate with a display control module 195. Display control interface 193 receive commands relating to the position and/or orientation of display 20, and transmit the commands to display control module 195. For example, display control interface 193 can receive commands generated by processing circuit 163 in response to user input received at touchscreens 110, 120 and/or sensors 280 via user input interface 173, and transmit the commands to display control module 195. Display control module 195 can receive the commands and control operation of display 20 (e.g., using actuation components for controlling/articulating display 20). In some embodiments, display control interface 193 transmits traverse, tilt, and/or swivel commands generated in response to user input received at touchscreens 110, 120, and display control module 195 electronically controls the position and/or orientation of display 20 based on the traverse, tilt, and/or swivel commands. In some embodiments, display control interface 193 transmits a command configured to deactivate electronic control of the position and/or orientation of display 20 generated in response to user input received at sensors 280, and display control module 195 deactivates electronic control (e.g., by decoupling actuation components from display 20), allowing for a user to manually adjust the position and/or orientation of display 20.

In various embodiments, display interface 171, user input interface 173, and/or display control interface 193 can be included in a single interface or module. For example, the same interface can be used to transmit visual information to be displayed on touchscreens 110, 120 and/or main screen 130, to receive user inputs from touchscreens 110, 120 and/or sensors 280, and to transmit position and/or orientation commands to control the position and/or orientation of display 20. In some embodiments, a first such combined interface can be used to communicate with ultrasound electronics module 26 and components thereof, and a second such combined interface can be used to communicate with display 26 and components thereof.

Figure 4:
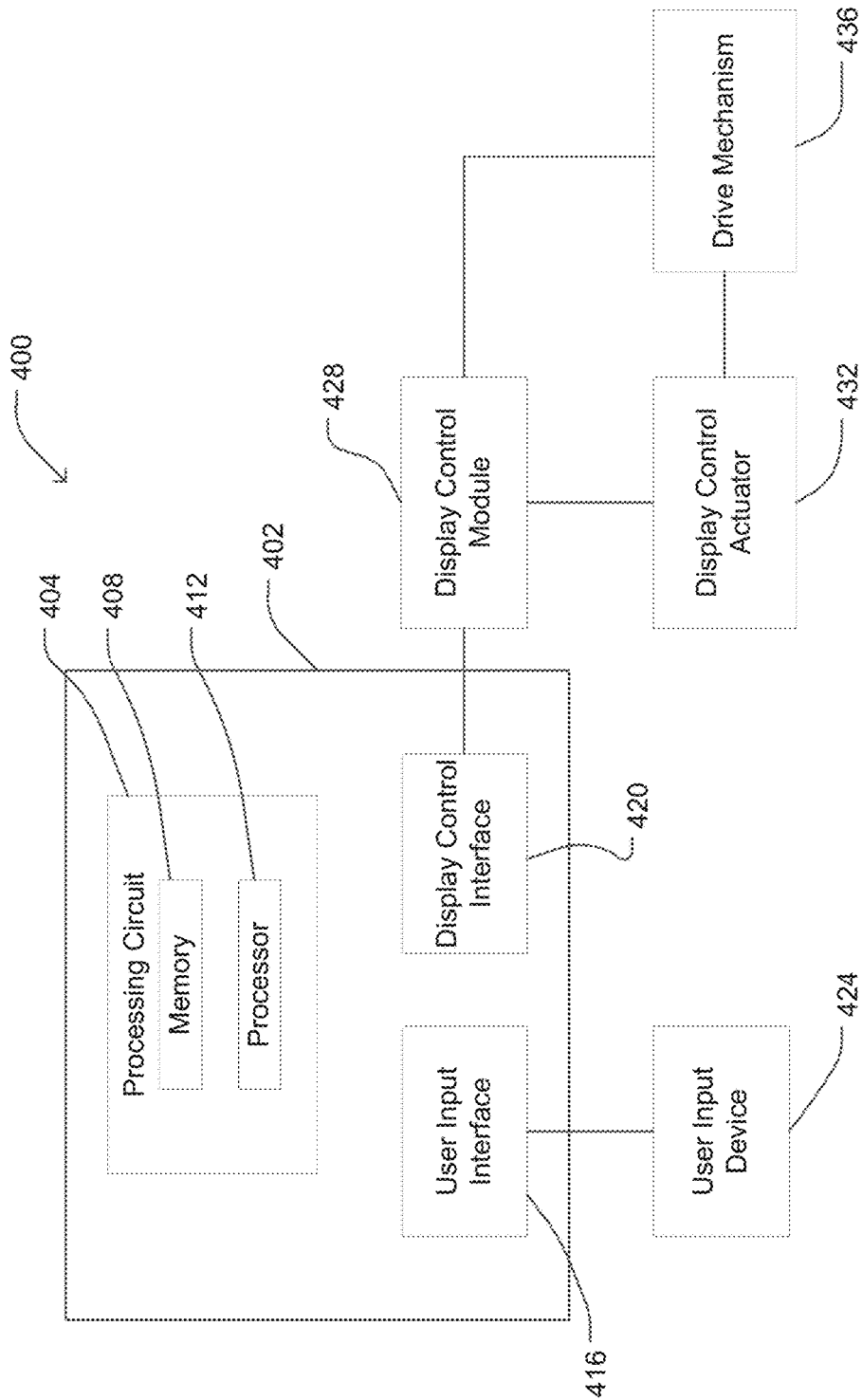
FIG. 4 illustrates a block diagram of various electronic components of a control system for controlling motion of a display of a portable ultrasound system according to an illustrative embodiment.

Referring now to FIG. 4, a block diagram of a control system 400 for controlling the position and/or orientation of display 20 is shown, in accordance with some embodiments. The illustrated components can be similar or identical to the components described with reference to FIG. 3. The control system 100 includes processing electronics 402. Processing electronics 402 may be similar to main circuit board 191 as shown in FIG. 3. Processing electronics 402 includes processing circuit 404 including memory 408 and processor 412, user input interface 416, and display control interface 420.

User input interface 416 is configured to receive user inputs from user input device 424. User input device 424 may be similar or identical to touchscreens 110, 120, keyboards, or other user input devices (e.g., other input devices shown in FIG. 2). User input device 424 may be similar or identical to sensors 280.

User input device 424 receives user input indicating a command from a user. For example, the user input can indicate a command to adjust a position and/or orientation of display 20, such as one or more of a traverse, tilt, or swivel command. Processing circuit 404 can receive the user input via user input interface 416 and generate an output command to transmit to control display 20 based on the command indicated by the user input. For example, processing circuit 404 can process the user input to determine that the user input indicates a command to shift the position of display 20 from a first side of platform 22 to a second side of platform 22 along a first axis, generate an output command based on the determination, and transmit the output command to display control module 428 via display control interface 420. Display control interface 420 receives output commands configured to control the position/orientation of display 20 and transmits the output commands to display control module 428. In some embodiments, a single command (e.g., a single gesture on a touch-sensitive interface) may be used to trigger movements in multiple directions. For example, a single swipe may be translated by processing circuit 404 into both traverse and swivel movement (e.g., based on a stored mapping of input to movements of display 20).

In some embodiments, processing circuit 404 provides advantageous modularity by being able to generate output commands based on user inputs received from touchscreens of any ultrasound electronics module 26. In other words, processing circuit 404 contains algorithms and instructions configured to process user input from a user input device of various ultrasound electronics modules 26, determine if the user input indicates one or more of a traverse, tilt, or swivel command, and generate an output command based on the determination. In some embodiments, ultrasound electronics module 26 is configured to process the user input to determine if the user input indicates one or more of a traverse, tilt, or swivel command.

Display control module 428 is configured to control the position/orientation of display 20. In some embodiments, display control module 428 is located in electronics of display 20. Display control module 428 may be associated with display electronics of display 20 for outputting display information via main screen 130. Display control module 428 is configured to transmit control commands to display control actuator 432 and/or drive mechanism 436. Display control module 428 may include processing electronics including a memory, such as a memory configured to store state information regarding whether drive mechanism 436 is coupled to display 20, and position/orientation information regarding a position and/or orientation of display 20 and/or drive mechanism 436 or components thereof. Display control module 428 can receive state information from display control actuator 432 and drive mechanism 436. In some embodiments, the state information can include a default or home position/orientation of display 20, and processing electronics 402 may be configured to cause display 20 to be placed in the home position/orientation in response to a reset command, a power up or power down of ultrasound electronics module 26, a predetermined amount of time expiring, etc. Such a home position may be configured to align display 20 with other components of the system such that, if display 20 is tilted forward, it may be mated and or locked into contact with a lower portion of the device for safe movement and/or storage.

In some embodiments, the drive mechanism 436 is configured to restrict motion about a tilt axis when the display 20 is outside of a center position along a traverse axis (e.g., to prevent the display 20 from being tilted down unless the display 20 is aligned in a proper position for stowing in the default position). In some embodiments, the drive mechanism 436 includes a cam or ramp configured to align the display 20 to a center position about a swivel axis when the display 20 is rotated to the default position. The cam or ramp may guide the display 20 about the swivel axis.

Display control actuator 432 is configured activate or deactivate electronic control/articulation of display 20. For example, display control actuator 432 may mechanically couple/decouple drive mechanism 436 from display 20 (e.g., engage/disengage drive mechanism 436 from display 20) in response to a couple/decouple command received from display control module 428. Display control actuator 432 may also interrupt an electronic connection (e.g., interrupt a circuit) between display control module 428 and drive mechanism 436, such as by receiving an interrupt command directly from display control interface 420. In some embodiments, display control actuator 432 is configured to default to maintaining drive mechanism 436 in an engaged state with display 20 unless a command is received with instructions to disengage drive mechanism 436 (e.g., a command generated and received based on user input received at sensors 280 to set drive mechanism 436 in a neutral state, to set drive mechanism 436 in a manual mode allowing a user to manually adjust the position and/or orientation of display 20, etc.). In some embodiments, sensors 280, or a portion thereof, may additionally or alternatively cause movement of display 20. For example, detecting of pressing or movement on or near a left side of display 20 may cause traverse movement in the left direction, and pressing or movement on or near a right side may cause movement in a right direction.

In some embodiments, disengaging the drive mechanism 436 from the display 20 may facilitate operating the display 20 in a free motion mode of operation. For example, the drive mechanism 436 can be configured to operate in a first mode in which the drive system is disengaged from the display 20, such that the display 20 is configured to move in response to receiving a force greater than a first force threshold. The drive mechanism 436 can be configured to operate in a second mode in which the drive mechanism 436 is engaged to the display 20, such that the display is configured to move in response to receiving a force greater than a second force threshold. The second force threshold is greater than the first force threshold. In some such embodiments, a user attempting to move the display 20 may perceive that the display 20 does not move while the drive mechanism 436 is engaged to the display 20 (e.g., the second force threshold is greater than a force at which the entire ultrasound system including the display 20 moves, rather than the display 20 moving relative to the remainder of the ultrasound system).

In some embodiments, processing electronics 402 may be configured to receive a user input from sensors 280 and control operation of drive mechanism 436 to control or assist motion of display 20 based on the command. For example, the user input may indicate one or more of a traverse, swivel, or tilt motion, and processing electronics 402 may be configured to engage (or maintain engagement) drive mechanism 436 with display 20, and cause drive mechanism 436 to provide traverse, tilt, and/or swivel output to display 20 based on the user input.

Drive mechanism 436 is configured to cause display 20 to change in position and/or orientation. For example, drive mechanism 436 may be located inside of a housing of platform 22 and be configured to be coupled (e.g., engaged) to display 20 or components thereof. Drive mechanism 436 can include one or more drives (e.g., motors, linear actuators, etc.) configured to apply forces to display 20 to adjust the position and/or orientation of display 20 in response to commands received via display control module 428. For example, drive mechanism 436 can be configured to translate display 20 along an axis (e.g., shift the position of display 20 side to side along a traverse axis), as well as to rotate display 20 about one or more axes (e.g., rotate the display 20 about a tilt axis and/or a swivel axis). In some embodiments, drive mechanism 436 includes a plurality of drives each dedicated to cause one of a traverse motion, a swivel motion, or a tilt motion.

For example, display control module 428 may receive a command from display control interface 420, the command including instructions to traverse display 20 to the left (based on a frame of reference of a user facing main screen 130 of display 20) by a certain distance and tilt display 20 by fifteen degrees towards platform 22. Display control module 428 controls operation of display control actuator 432 to engage drive mechanism 436 to display 20. Display control module 428 controls drive mechanism 436 to cause the desired traverse and tilt of display 20.

In another example, display control module 428 may receive a command from display control interface 420, the command including instructions to decouple drive mechanism 436 from display 20. In some embodiments, display control module 428 transmits a command to display control actuator 432 configured to mechanically disengage drive mechanism 436 from display 20. In some embodiments, display control actuator 432 directly receives an interrupt command from display control interface 420 to interrupt an electronic connection between display control module 428 and drive mechanism 436.

In some embodiments, the sensors 280 are configured to detect at least one of a force or a direction associated with the user input. The display control module 428 can cause a force-assisted movement of the display 20 based on the user input detected by the sensors 280. For example, the display control module 428 can cause movement of the display 20 based on the detected force being greater than a force threshold. The display control actuator 432 can cause the drive mechanism 436 to move the display 20 (e.g., traverse, tilt, or swivel the display 20) in a direction corresponding to the detected direction (e.g., move in the same direction; move in a direction determined based on decomposing the detected direction into movement along or about at least one of a traverse axis, a swivel axis, or a tilt axis as described with reference to FIG. 5). In some such embodiments, the display control module 428 can enable a force-assisted movement, such that a user applying a force to the sensors 280 perceives the display 20 to move together with the force applied by the user. For example, the display control actuator 432 can be configured to cause the display 20 to move within a predetermined time after the sensors 280 receive the user input.

Figure 5:
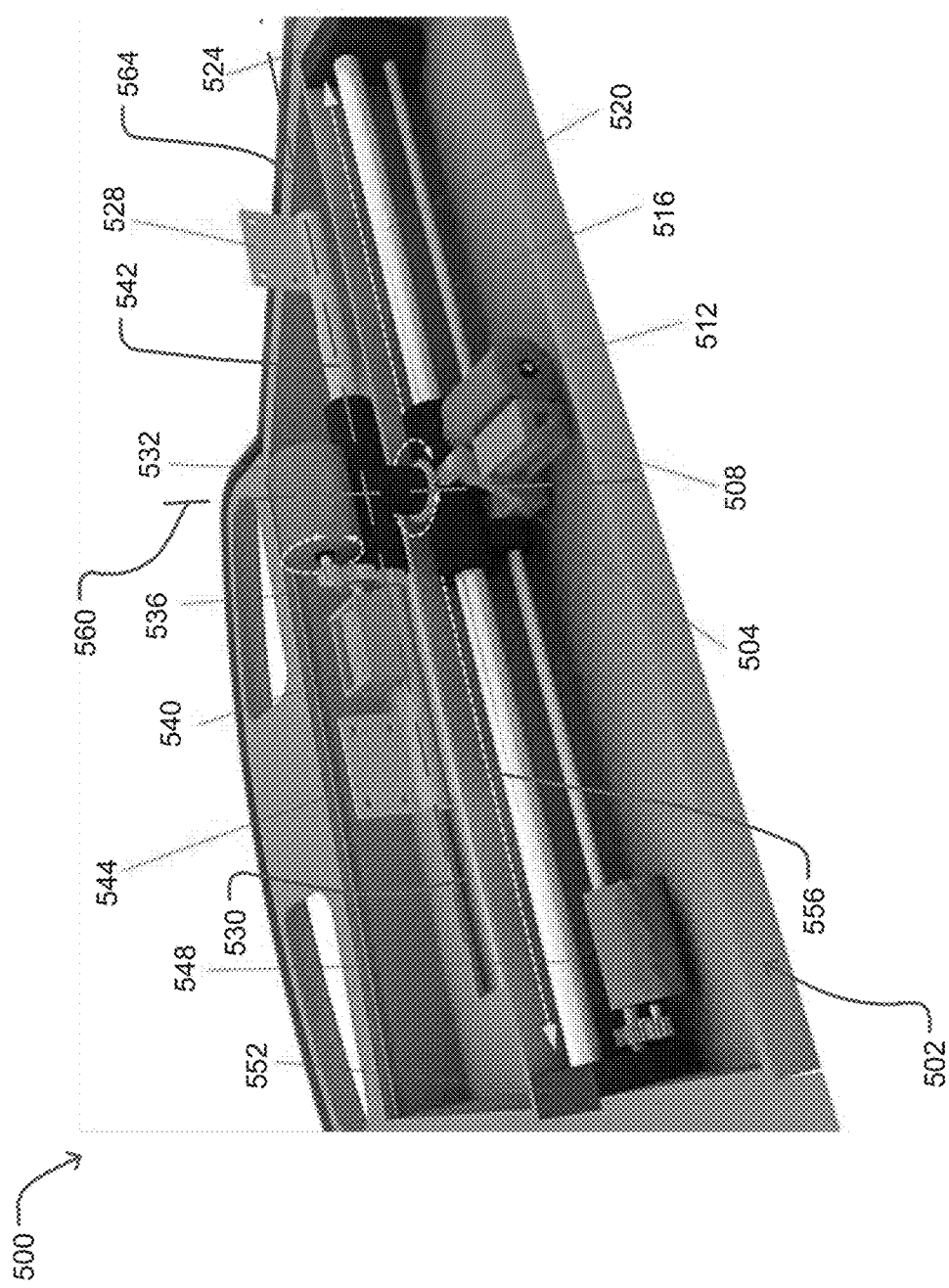
FIG. 5 illustrates a perspective view of a drive system for driving motion of a display of a portable ultrasound system according to an illustrative embodiment.
Figure 6:
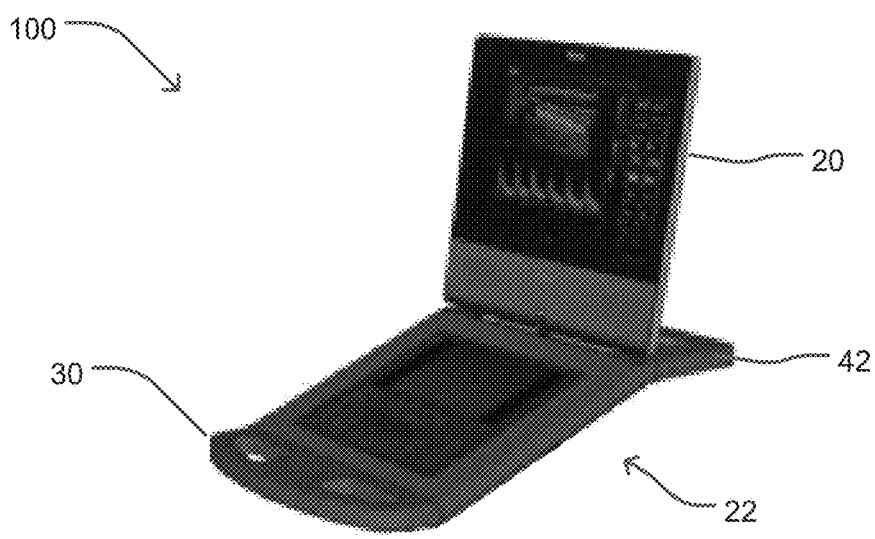
FIG. 6 illustrates a perspective view of a portable ultrasound system according to an illustrative embodiment.
Figure 7:
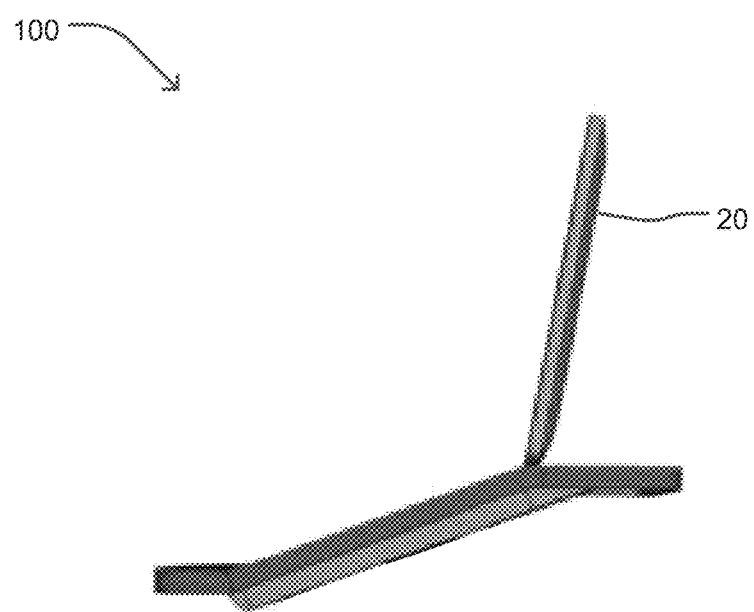
FIG. 7 illustrates a side view of a portable ultrasound system according to an illustrative embodiment.
Figure 8:
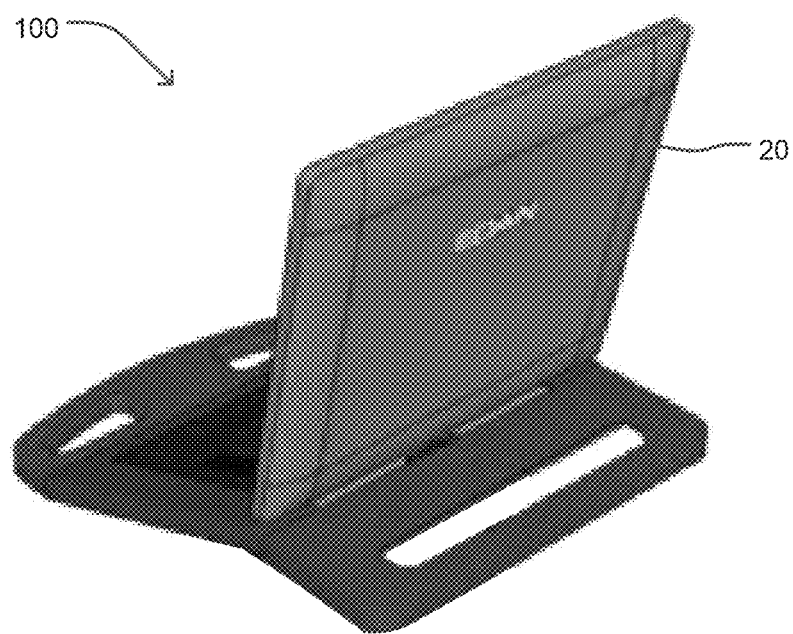
FIG. 8 illustrates a rear perspective view of a portable ultrasound system according to an illustrative embodiment.
Figure 9:
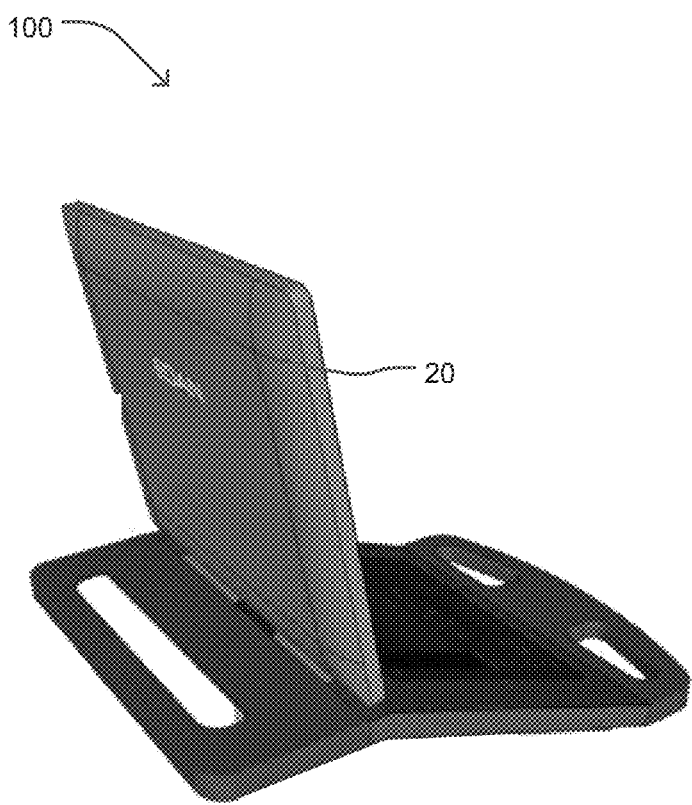
FIG. 9 illustrates a detailed perspective view of a portable ultrasound system according to an illustrative embodiment.
Figure 10:
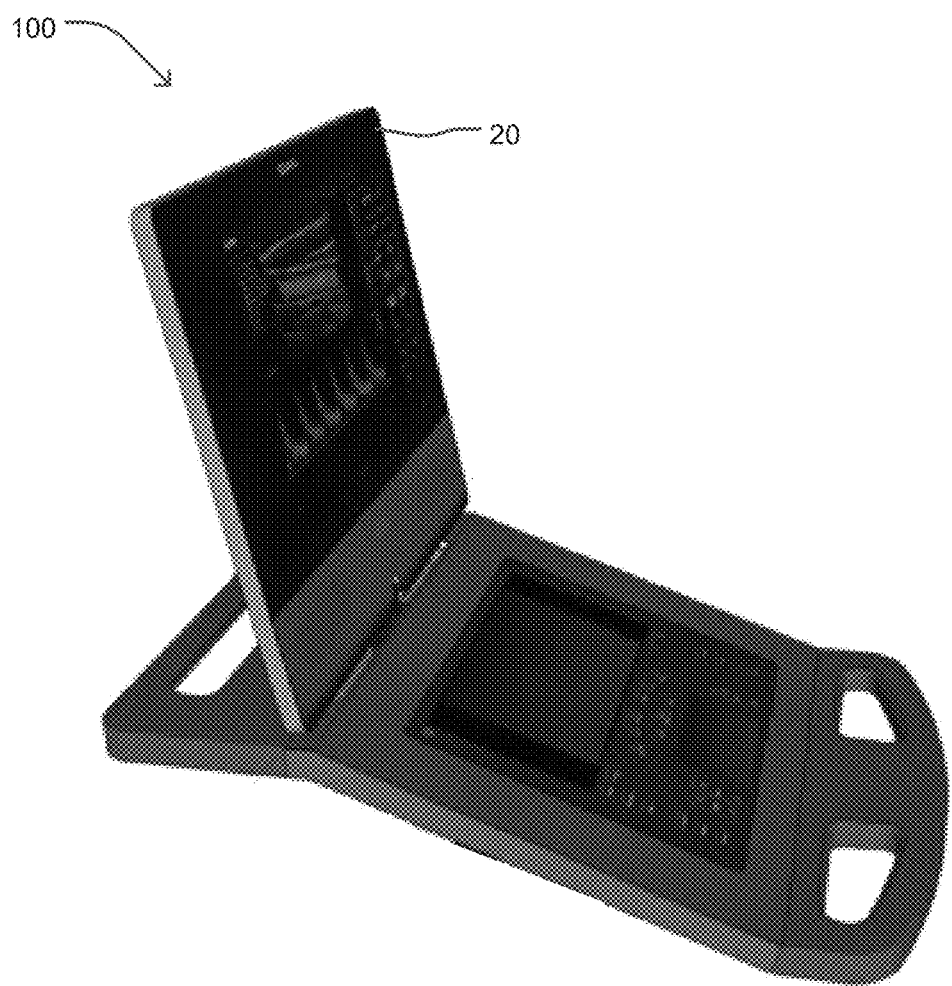
FIG. 10 illustrates a detailed side view of a portable ultrasound system according to an illustrative embodiment.
Figure 11:
FIG. 11 illustrates a detailed perspective view of a portable ultrasound system with a partially closed display according to an illustrative embodiment.
Figure 12:
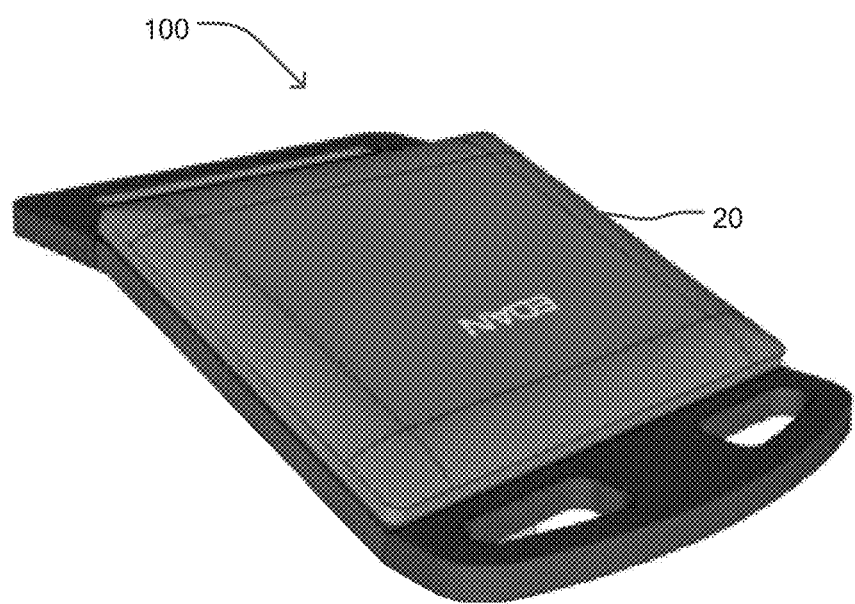
FIG. 12 illustrates a detailed perspective view of a portable ultrasound system with a closed display according to an illustrative embodiment.
Figure 13:
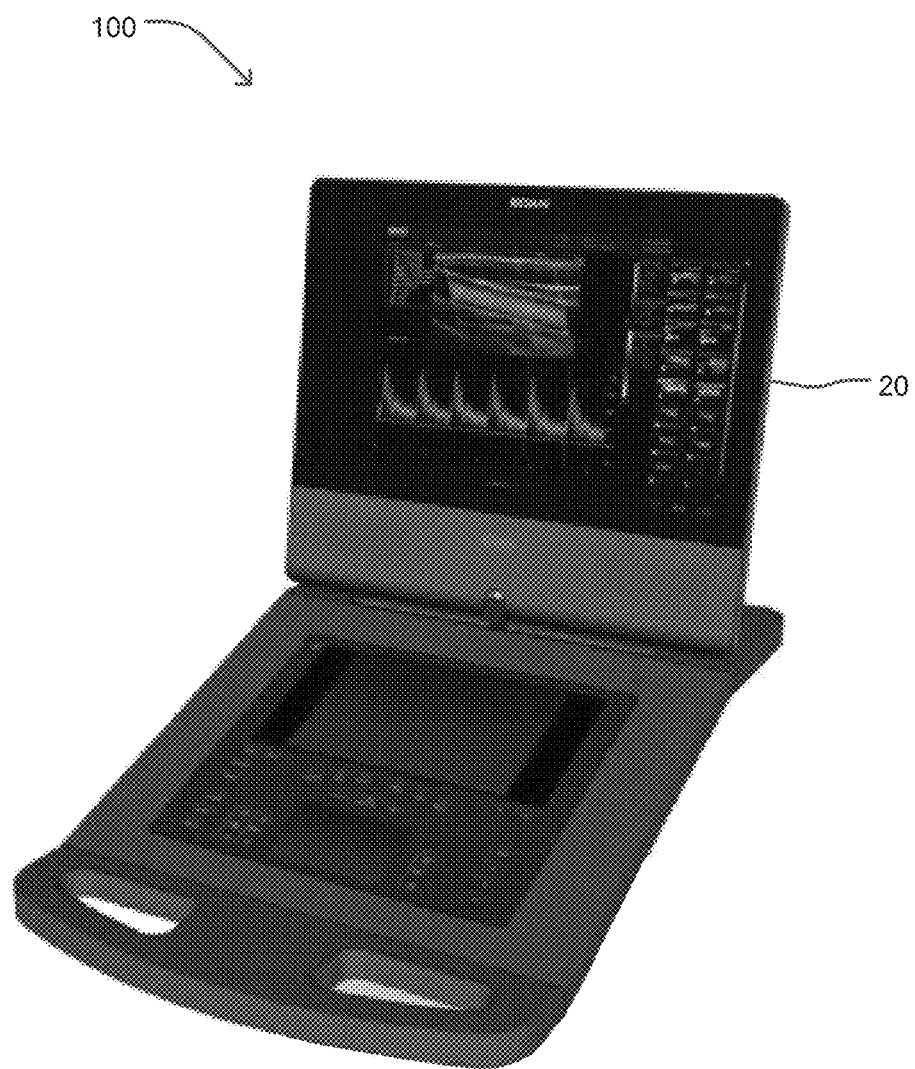
FIG. 13 illustrates a detailed perspective view of a portable ultrasound system with a display in a home position according to an illustrative embodiment.

Referring now to FIG. 5, drive system 500 for controlling the position and/or orientation of display 20 is shown in accordance with one embodiment. Drive system 500 can include various components similar or identical to those illustrated in FIG. 4, such as drive mechanism 436.

Drive system 500 can be mechanically attached to display 20, such as by using display frame mount 542. Display frame mount 542 includes attachment members 528, 544 which can be mounted to (e.g., inside of) display 20. Other components of drive system 500 can be located inside of housing 502 of platform 22, providing a compact form factor in which all components for controlling the position and/or orientation are located internally in portable ultrasound system 100. Display frame mount 542 includes a rod located along first axis 564, such that rotation of the display frame mount 542 about the first axis 564 causes display 20 to tilt. The rod of display frame mount 542 can rotate within a track 530.

In some embodiments, rotation of the display frame mount 542 about first axis 564 is caused by a drive, such as tilt motor 532. Tilt motor 532 can be an electric motor with an integrated power supply (e.g., battery) or power received from an external power supply (e.g., via power supply board 179). Tilt motor 532 can be connected via gears to a drive gear fixed to the rod of display frame mount 542, such that rotation of the drive gear about first axis 564 causes display frame mount 542 to be rotated about first axis 564. First axis 564 is oriented parallel to and within a plane defined by display 20, such that rotation about first axis 564 causes display 20 to rotate towards or away from platform 22 and ultrasound electronics module 26 (e.g., to tilt).

In some embodiments, an actuator is used to control engagement of tilt motor 532 to display frame mount 542. For example, tilt solenoid 540 can receive an engage or disengage signal, and based on the signal, mechanically engage tilt motor 532 to display frame mount 542, such as by positioning a gear to engage a gear coupled to a rotor of tilt motor 532 and a drive gear of display frame mount 542.

Drive system 500 may similarly include combinations of drives and actuators for causing translation and/or rotation of display frame mount 542 relative to other axes. As shown in FIG. 5, drive system 500 includes traverse motor 548 configured to rotate traverse drive rod 516 in order to convert rotational motion of traverse drive rod 548 into translation of display frame mount 542 along second axis 556. Second axis 556 may be parallel to first axis 542. Display frame mount 542 may be positioned on guide rail 520 located parallel to second axis 556, guiding translation (e.g., for traversal of display 20) along guide rail 520. Mounting blocks 524, 552 may be provided at either end of guide rail 520 to support drive system 500.

As shown in FIG. 5, drive system 500 includes swivel motor 512. Swivel motor 512 may be oriented transverse to second axis 556, such that rotation of a gear coupled to a rotor of swivel motor 512 can cause display frame mount 542 to rotate about third axis 560. Third axis 560 may be oriented in a plane defined by display 20 and oriented perpendicular to first axis 542 and second axis 556. Rotation about third axis 560 may cause display 20 to swivel (e.g., in a frame of reference of a user facing display 20, a left edge of display 20 moves towards the user while a right edge of display 20 moves away from the user or vice versa).

Drive system 500 includes at least one actuator configured to couple/decouple traverse motor 548 and swivel motor 512 from display frame mount 542. As shown in FIG. 5, second solenoid 508 is configured to position one or more gears in between gears mechanically coupled to traverse motor 548 and swivel motor 512 and gears mechanically coupled to display frame mount 542, such as in response to an engage or disengage signal. In some embodiments, separate actuators are provided for engaging or disengaging each of traverse motor 548 and swivel motor 512.

Figure 20A:
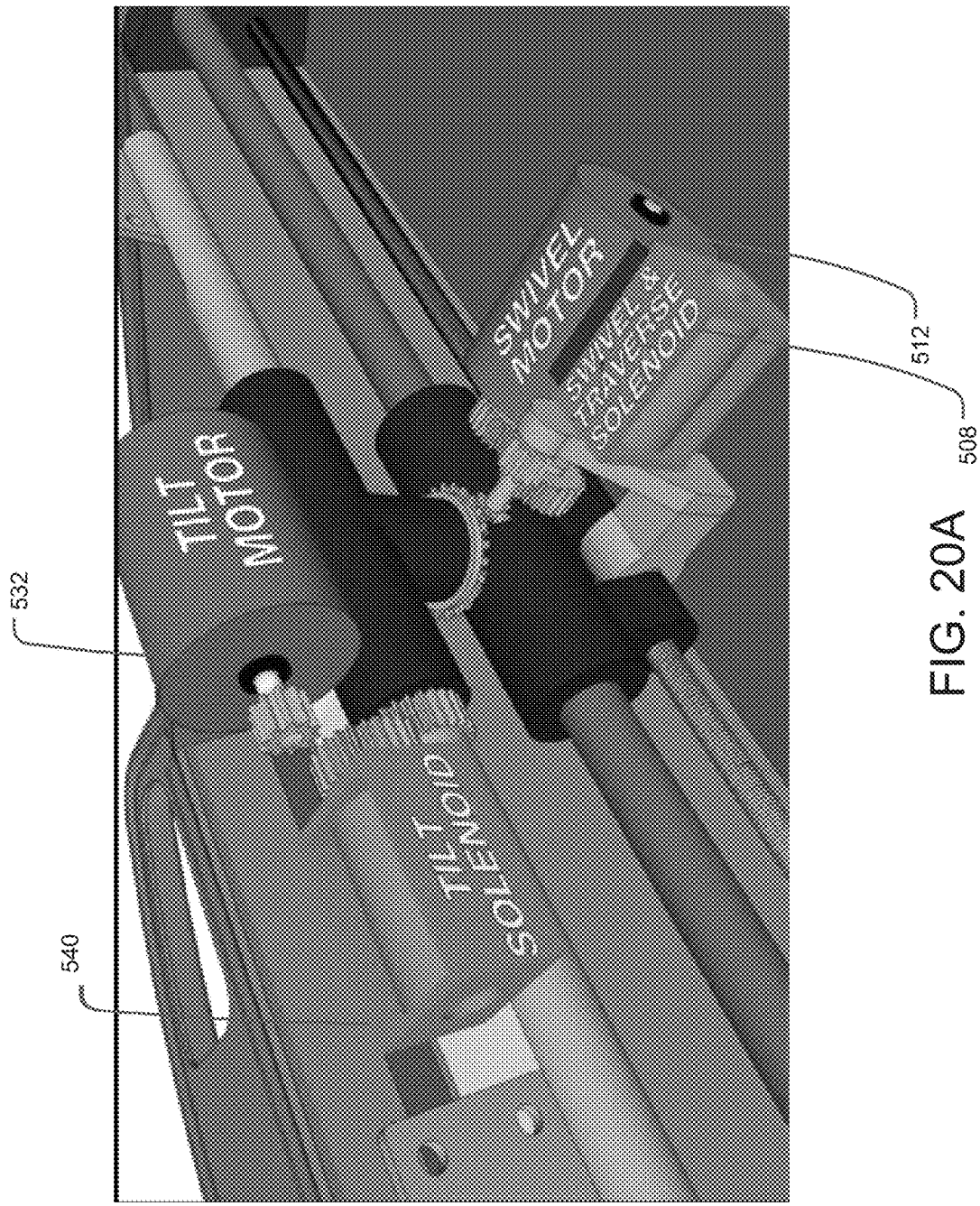
FIG. 20A illustrates a detailed perspective view of a drive mechanism disengaged from a display frame mount according to an illustrative embodiment.
Figure 20B:
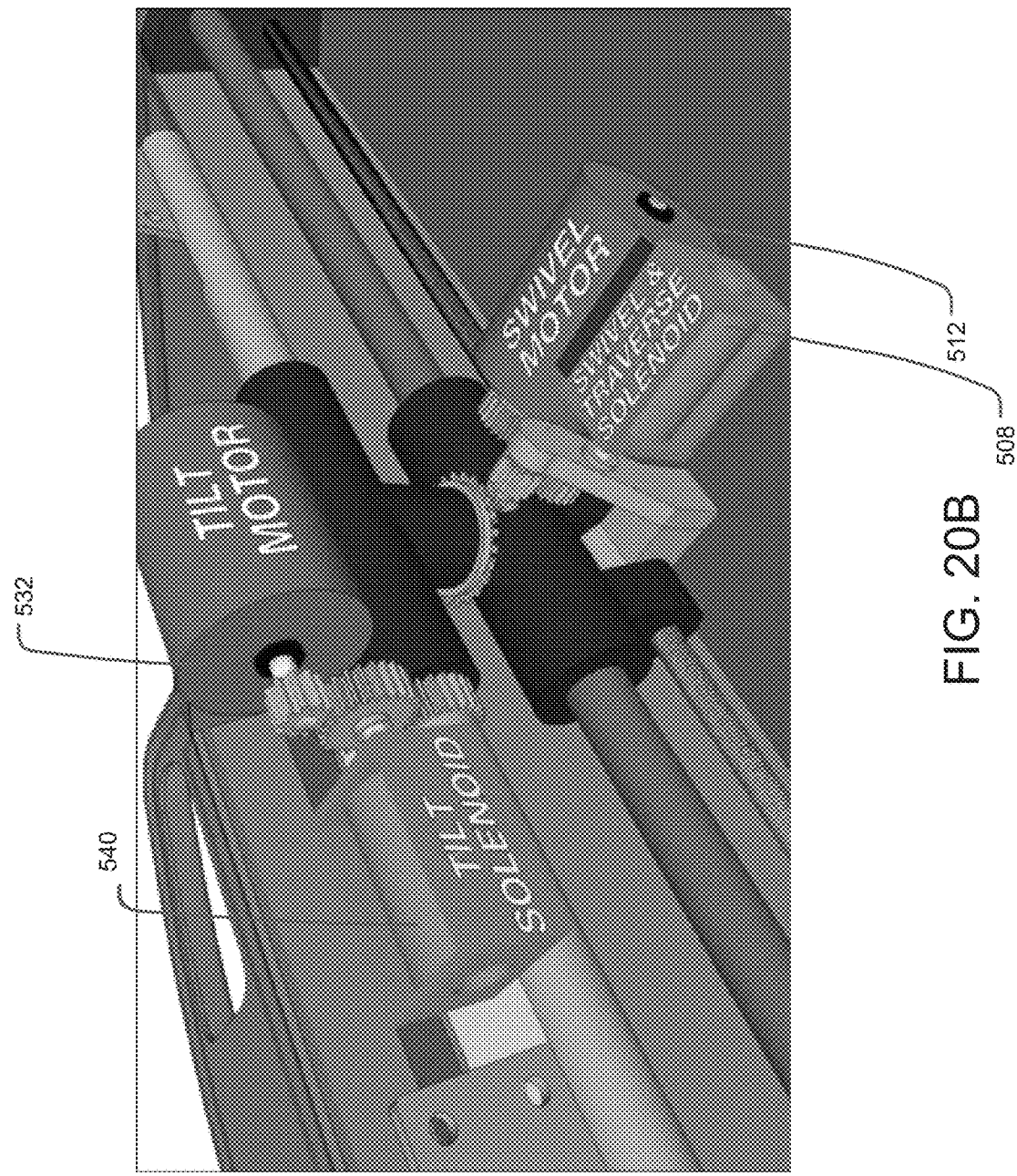
FIG. 20B illustrates a detailed perspective view of the drive mechanism of FIG. 20A engaged to a display frame mount according to an illustrative embodiment.

For example, and as shown in further detail in FIGS. 20A-20B, in response to engage or disengage signals/commands, actuators such as tilt solenoid 540 and second solenoid 508 can mechanically engage or disengage drives (e.g., tilt motor 532, traverse motor 548, swivel motor 512) from display frame mount 542.

In some embodiments, the drive system 500 is configured to automatically align the display 20 in a default position. For example, the drive system 500 can translate the display 20 to a center position along the second axis 556, rotate the display 20 to a center position about the third axis 560, and subsequent to the translation along the second axis 556 and rotation about the third axis 560, rotate the display 20 about the first axis 564 towards the platform 22, such as to stow the display 20 in the default position. The automatic alignment may be performed in response to conditions such as a command, a reset, an indication of a power up or power down, or other conditions as described herein.

While FIG. 5 illustrates the components of drive system 500 located and oriented in certain positions, these positions/orientations may be altered in various ways, and rotational elements such as gears may be used to convert the direction, angle, or orientation of mechanical output of drives of drive system 500 into corresponding movement of display 20 as desired.

Referring now to FIGS. 6-12, portable ultrasound system 100 is illustrated in various perspectives. In some embodiments, a frame of reference is associated with portable ultrasound system 100 as viewed by a user facing display 20, such that handles 30 are positioned in a front region of portable ultrasound system 100, handles 42 are positioned in a rear region of portable ultrasound system 100, and display 20 is configured to traverse from left to right, tilt towards or away from platform 22 (e.g., tilt down/towards platform 22 to close display 20, tilt up/away from platform 22 to open display 20, etc.), or swivel clockwise/counterclockwise to angle display 20 relative the frame of reference. For example, as shown in sequence from FIG. 10 to FIG. 12, display 20 is tilted down from a relatively open position to a closed position. In various embodiments, portable ultrasound system 100 may be described using various other frames of reference.

Figure 14:
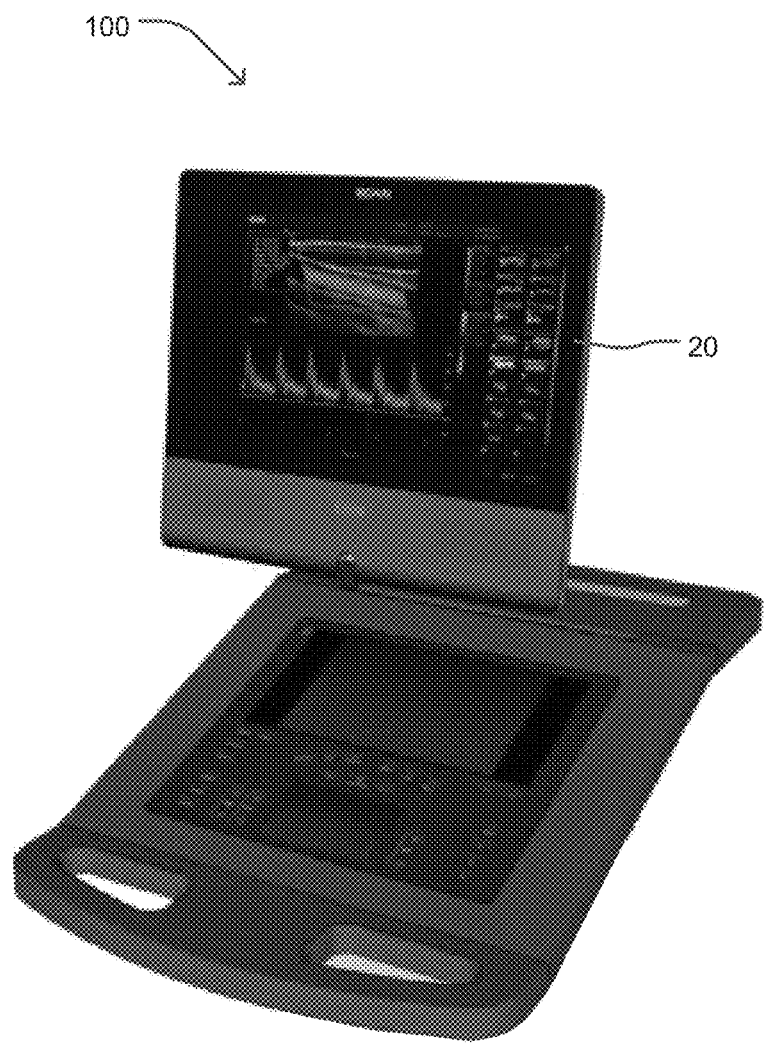
FIG. 14 illustrates a detailed perspective view of the display of FIG. 13 traversed to a left side position according to an illustrative embodiment.
Figure 15:
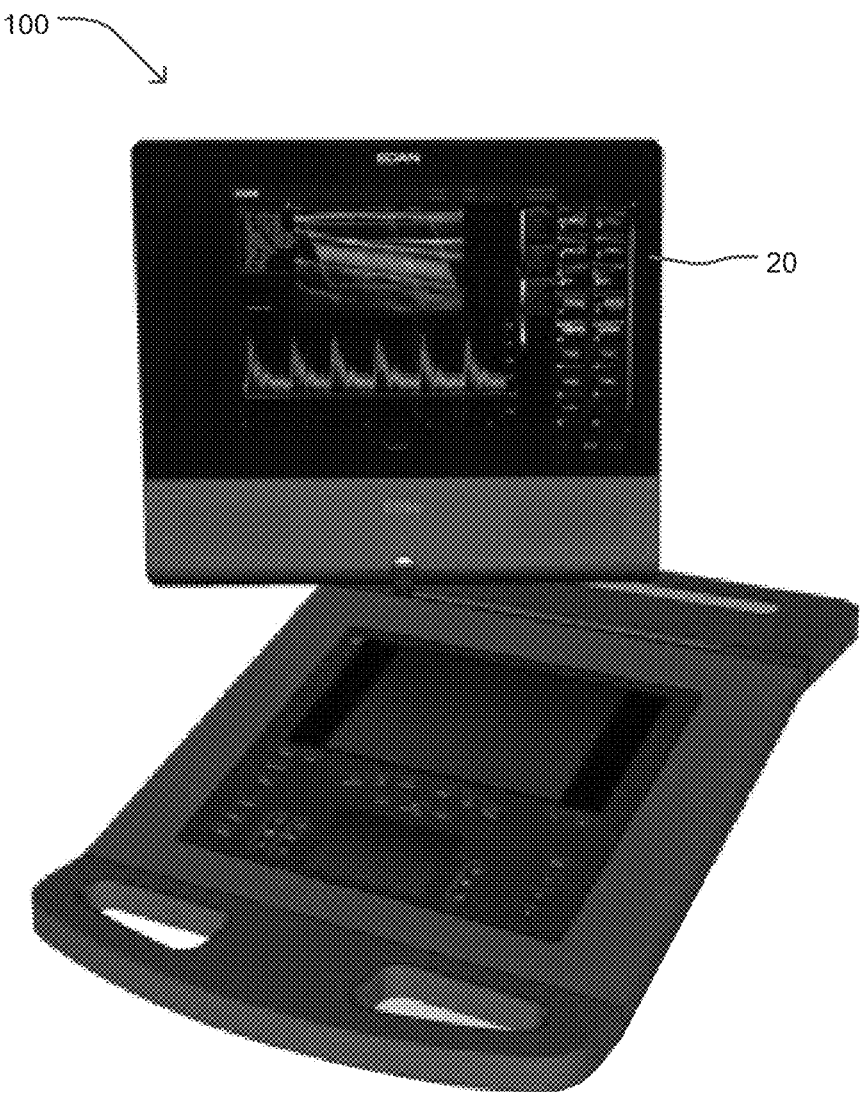
FIG. 15 illustrates a detailed perspective view of the display of FIG. 14 swiveled counterclockwise according to an illustrative embodiment.
Figure 16:
FIG. 16 illustrates a detailed perspective view of the display of FIG. 15 swiveled further counterclockwise according to an illustrative embodiment.
Figure 17:
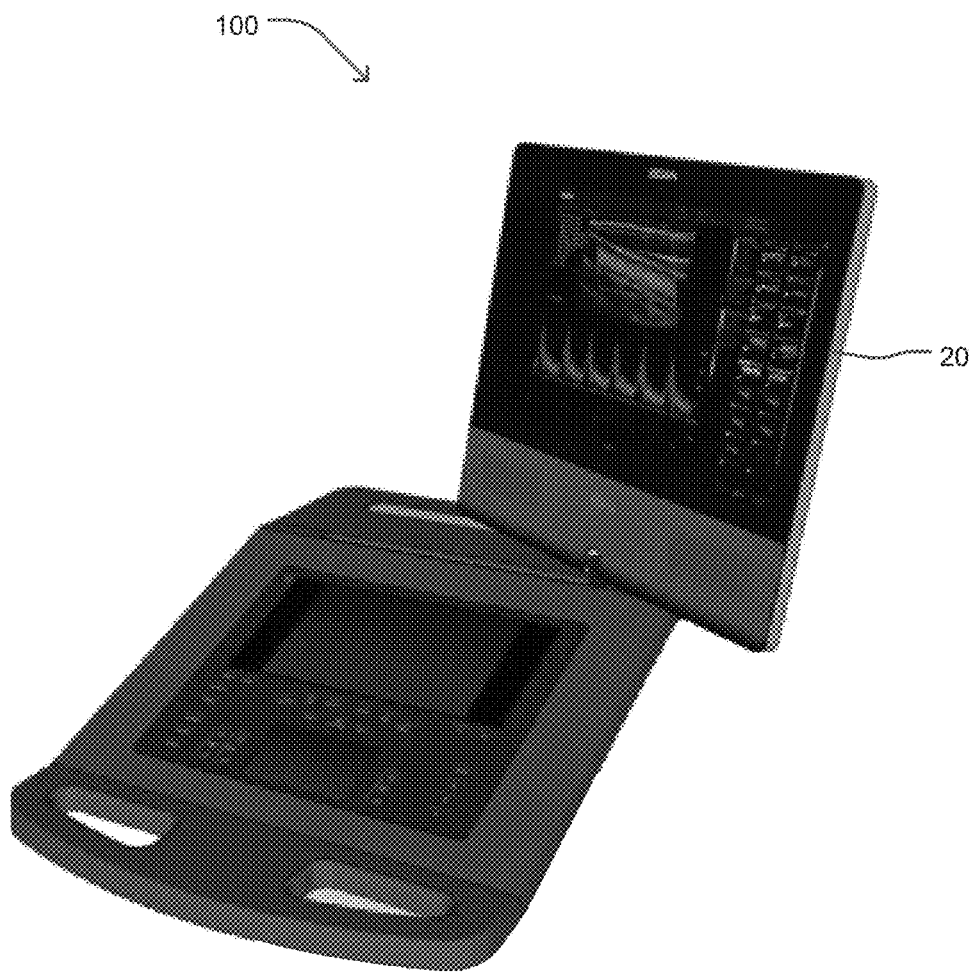
FIG. 17 illustrates a detailed perspective view of the display of FIG. 13 traversed to a right side position and swiveled clockwise according to an illustrative embodiment.

Referring now to FIGS. 13-16, portable ultrasound system 100 is shown in accordance with an embodiment in which traverse and swivel motions have been performed. As shown in FIG. 14, display 20 has been traversed to the left (e.g., traversed along second axis 556 illustrated in FIG. 5). For example, a user may have provided a command to traverse the display 20 to the left, or manually repositioned display 20, such as if the user was located on a left side of portable ultrasound system 100 and desired display 20 to be closer to the user. As shown in FIG. 15, display 20 has been swiveled counterclockwise, such that a left edge of display 20 is located more close to handles 30, and a right edge of display 20 is located more distance from handles 30. In other words, an angle in the plane of platform 22 between platform 22 and display 20 is increased between the left edge of display 20 and platform 22 in one direction and between the right edge of display 20 and platform 22 in an equal and opposite direction. As shown in FIG. 16, display 20 has been tilted further clockwise (e.g., the angles between the edges of display 20 and platform 22 are greater in FIG. 16 than in FIG. 15). As shown in FIG. 17, display 20 has been reoriented towards the right side of portable ultrasound system 100 and also swiveled clockwise. For example, a user may desire to orient display 20 such that display 20 faces the user (who may be positioned on a side of portable ultrasound system 100) with ultrasound electronics module 26 positioned between the user and display 20, such that the user can easily manipulate ultrasound electronics module 26, touchscreens 110, 120, etc., while viewing display 20. According to various implementations, each of the positions illustrated in FIGS. 13-16 may be achieved in an automated fashion based on user input and/or manually by the user (e.g., after receiving input causing disengagement of the drive system).

Figure 18:
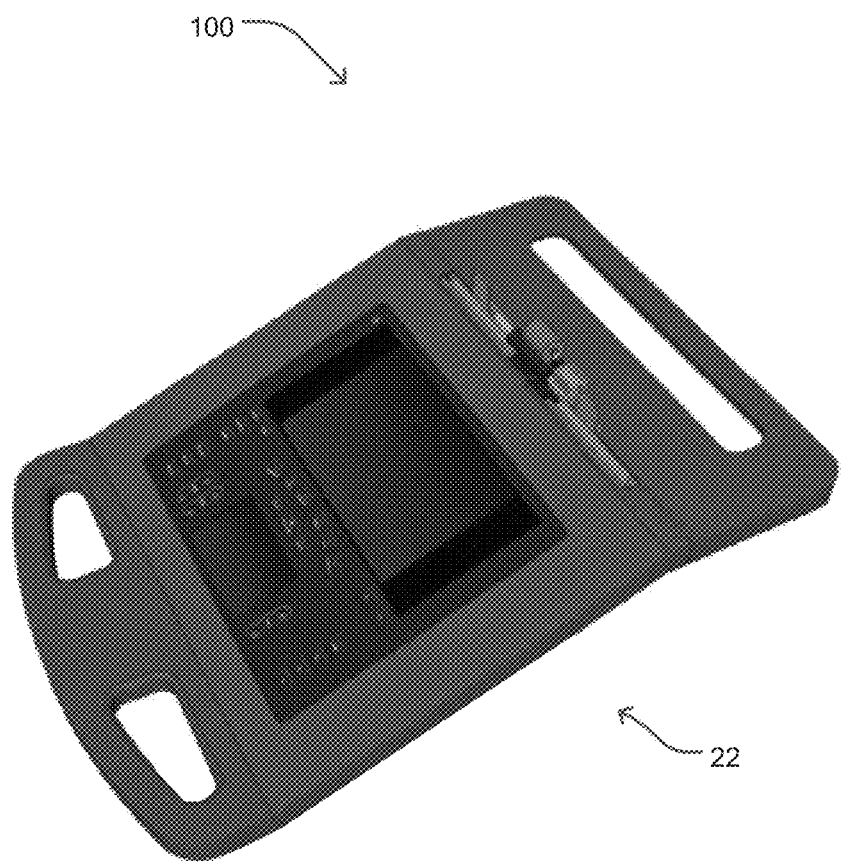
FIG. 18 illustrates a perspective view of a portable ultrasound system with a display removed according to an illustrative embodiment.
Figure 19:
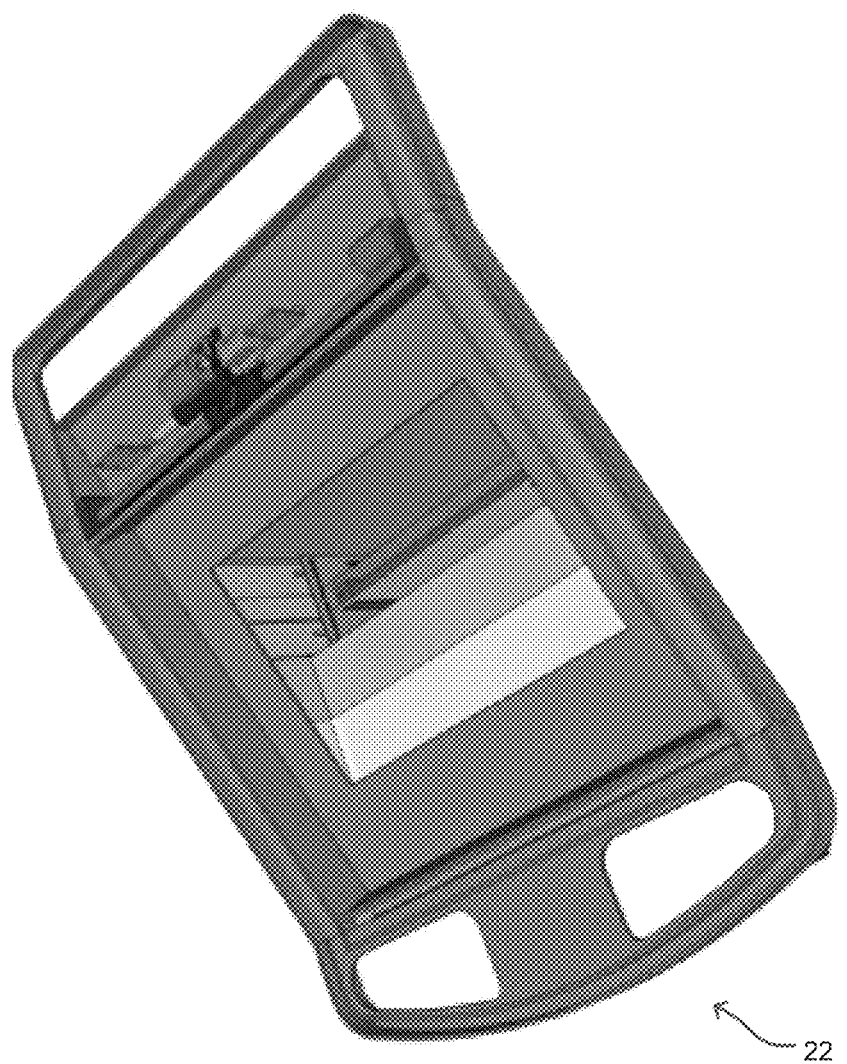
FIG. 19 illustrates a perspective view of a portable ultrasound system with various components removed according to an illustrative embodiment.
Figure 21:
FIG. 21 illustrates a perspective view of a portable ultrasound system with an ultrasound electronics module removed according to an illustrative embodiment.

Referring now to FIGS. 18-19 and 21, various embodiments and configurations of portable ultrasound system 100 are illustrated, showing modular features of portable ultrasound system 100. As shown in FIG. 18, display 20 has been removed to illustrate a drive system for controlling the position/orientation of display 20 (e.g., using drive system 500 shown in FIG. 5, etc.). Components of the drive system are contained within platform 22 (e.g., within housing 502 shown in FIG. 5, etc.), while display frame mount 542 can be contained within display 20, providing an elegant and compact form factor. For example, as shown in FIGS. 6-17, display 20 can be directly attached to platform 22 via the drive system and display 20 can be traversed, tilted, and swiveled using components internal to platform 22 and display 20.

As shown in FIGS. 19 and 21, ultrasound electronics module 26 has been removed from its position in platform 22. The interior of platform 22 can include electronics configured to be coupled to ultrasound electronics module 26 and/or display electronics, to provide communications, power, etc., to various components of portable ultrasound system 100. As such, portable ultrasound system 100 can include advantageous modularity features allowing for ultrasound electronics module 26 to be replaced, upgraded, or otherwise modified.

Referring now to FIGS. 22A-24B, ultrasound electronics module 26 is configured to be modular in accordance with one embodiment. Ultrasound electronics module 26 may include a self-contained housing for containing electronic components. Ultrasound electronics module 26 may include an ultrasound electronics assembly, an external cover of the user interface, and a rubber interface console. The cover and rubber interface console may be merged together to create a seal to prevent liquid ingress into the electronics assembly. Portable ultrasound system 100 may include an alignment system to guide ultrasound electronics module 26 into a track of a cavity of housing 502 of platform 22. As ultrasound electronics module 26 slides in the track, it reaches a stop position that utilizes a pivot feature to allow ultrasound electronics module 26 to be lowered into the cavity. As ultrasound electronics module 26 is lowered into the cavity, ultrasound electronics module 26 intercepts a latch mechanism that allows ultrasound electronics module 26 to engage a latch (e.g., a spring loaded latch). In response to pressure applied to ultrasound electronics module 26, the latch snaps over a locking feature to hold ultrasound electronics module 26 in place. In some implementations, ultrasound electronics module 26 and/or platform 22 may include electronic interfaces configured to mate with one another (e.g., upon latching module 26 in place), which may allow electronic components of module 26 and platform 22 to communicate with one another.

In some embodiments, a release mechanism is provided. For example, a latch handle may be located external to the module. In response to pressure applied by a user (e.g., a squeeze motion), the latch is released, pivoting ultrasound electronics module 26 upward, exposing grasp features on edges of ultrasound electronics module 26 allowing ultrasound electronics module 26 to be grasped and slid out of the tracks and out of platform 22.

Figure 22B:
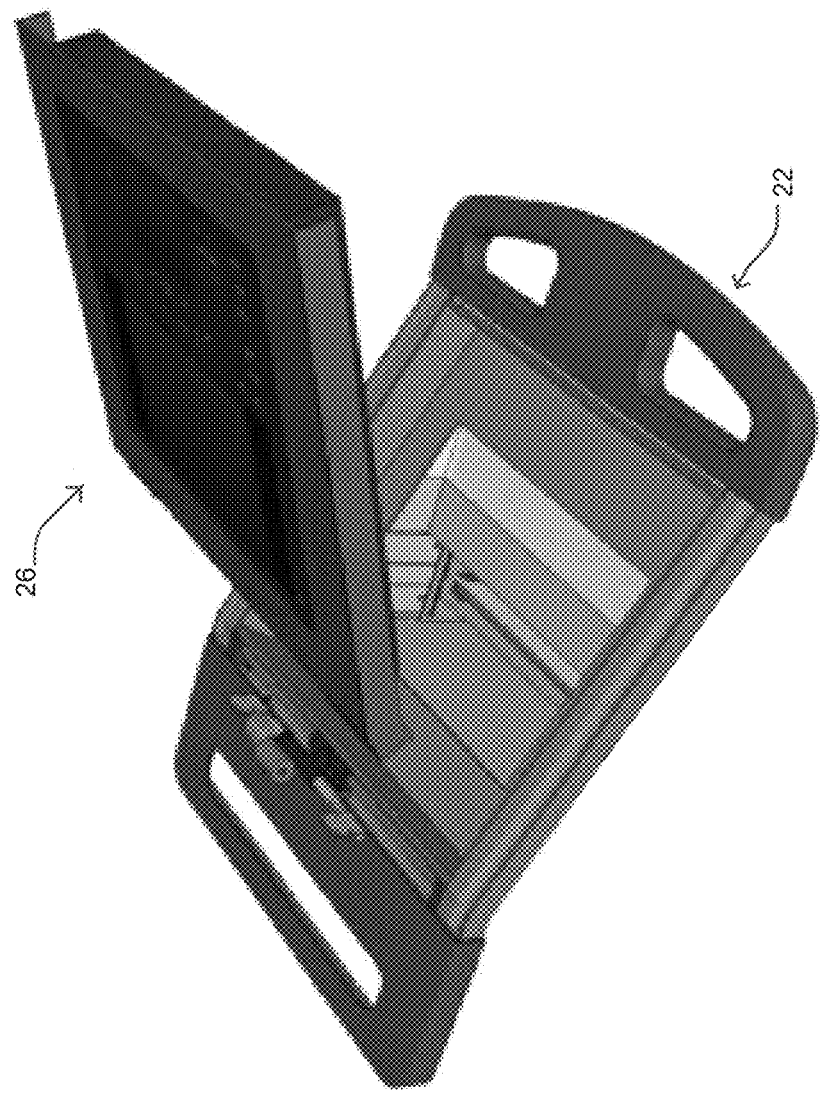
Figure 23A:
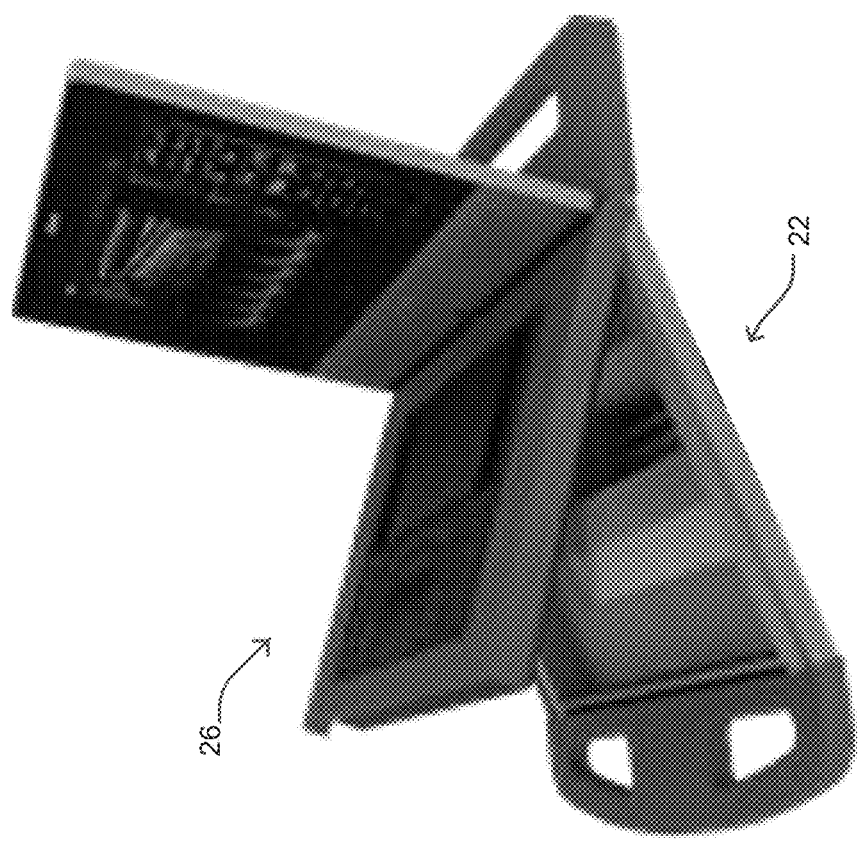
FIGS. 23A-23B illustrate perspective views of a portable ultrasound system with an ultrasound electronics module to be latched into the portable ultrasound system according to an illustrative embodiment.
Figure 23B:
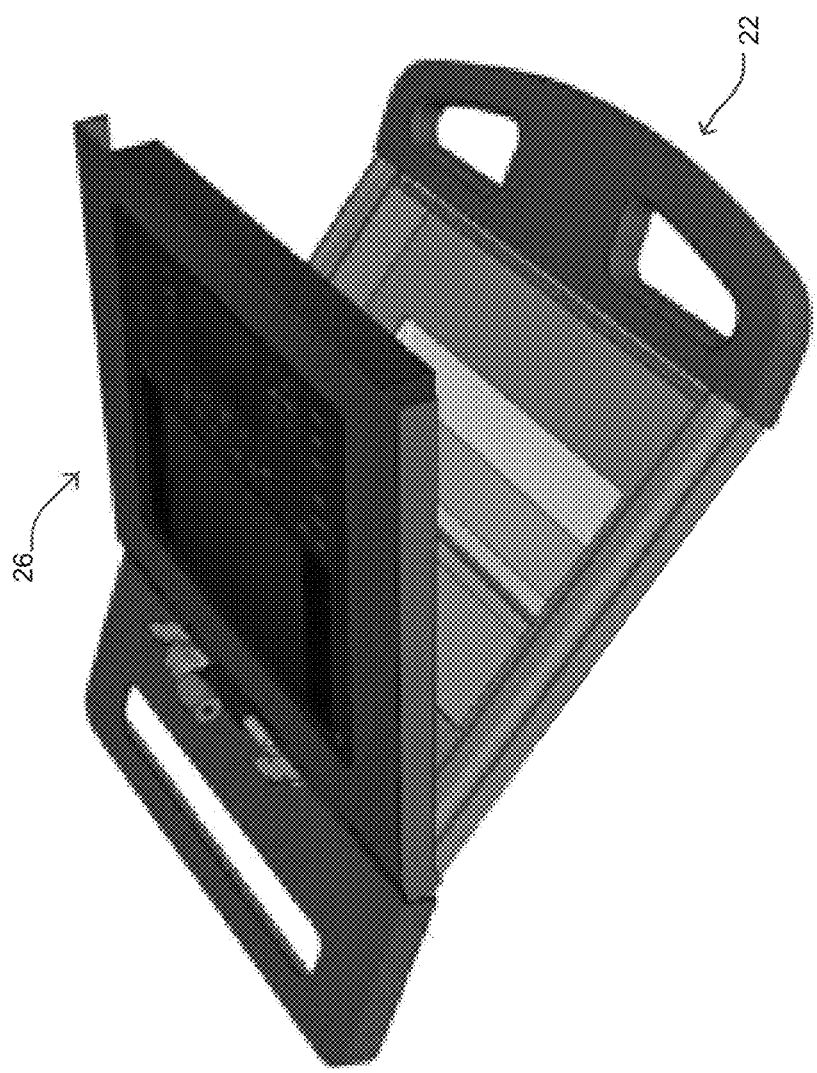
Figure 24A:
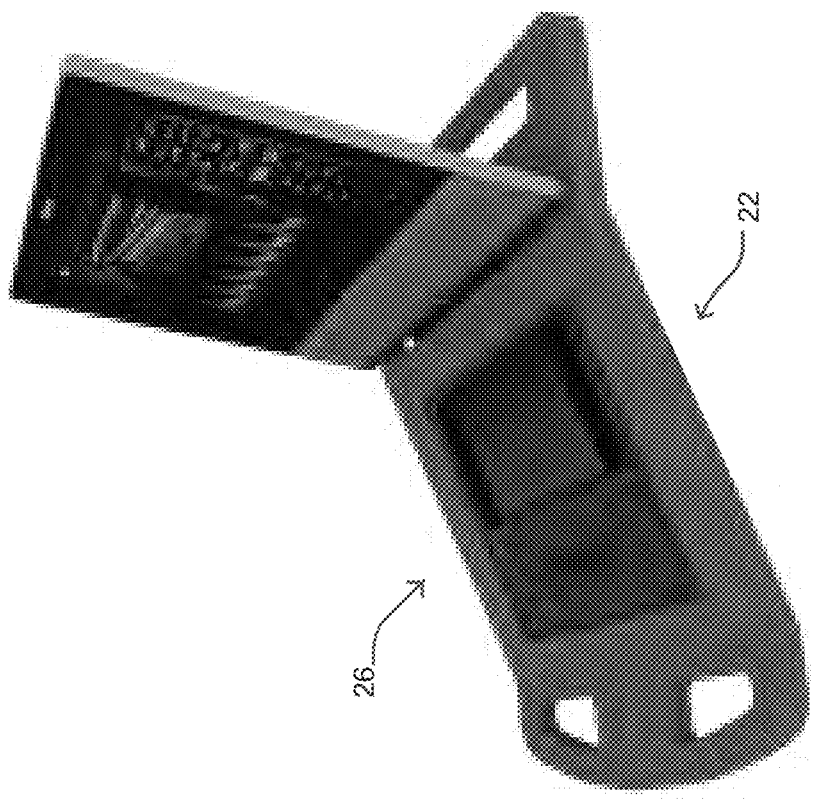
FIGS. 24A-24B illustrate perspective views of a portable ultrasound system with an ultrasound electronics module received in the portable ultrasound system according to an illustrative embodiment.
Figure 24B:

As shown in FIGS. 22A-22B, ultrasound electronics module 26 is positioned outside of platform 22. As shown in FIGS. 23A-23B, ultrasound electronics module 26 is positioned to contact a portion of platform 22 adjacent to display 20 such that ultrasound electronics module 26 may be pivoted into place. As shown in FIGS. 24A-24B, ultrasound electronics module 26 has been pivoted and latched into place. In some embodiments, pivoting and latching ultrasound electronics module 26 into place also cause electronic coupling between ultrasound electronics module 26 and other electronic components of portable ultrasound system 100.

Figure 25:
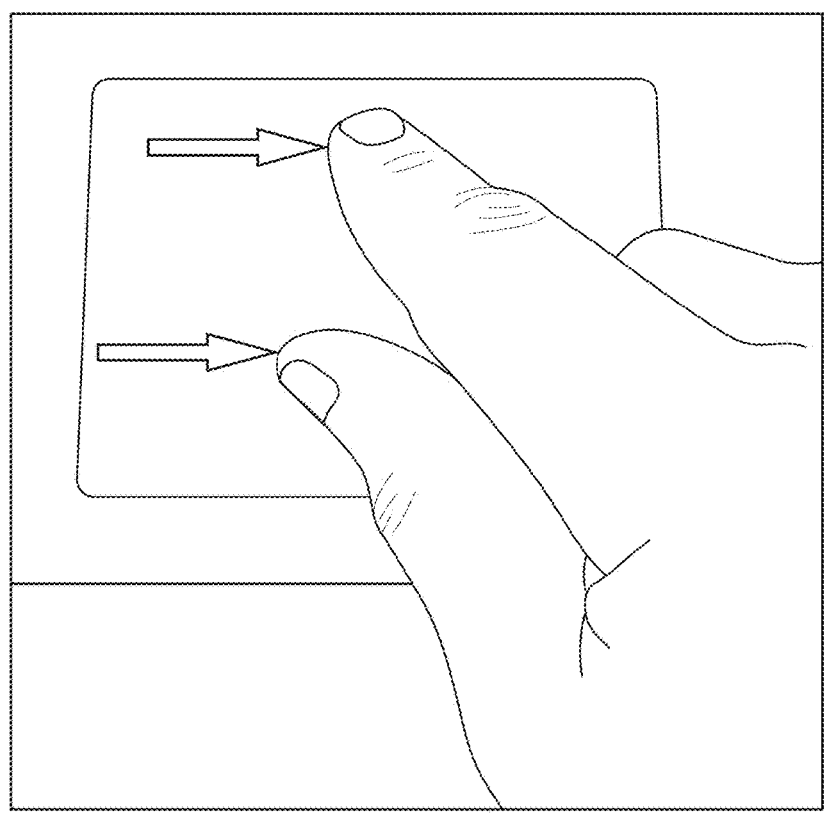
FIG. 25 illustrates a diagram of a traverse motion input at a user input device according to an illustrative embodiment.
Figure 26:
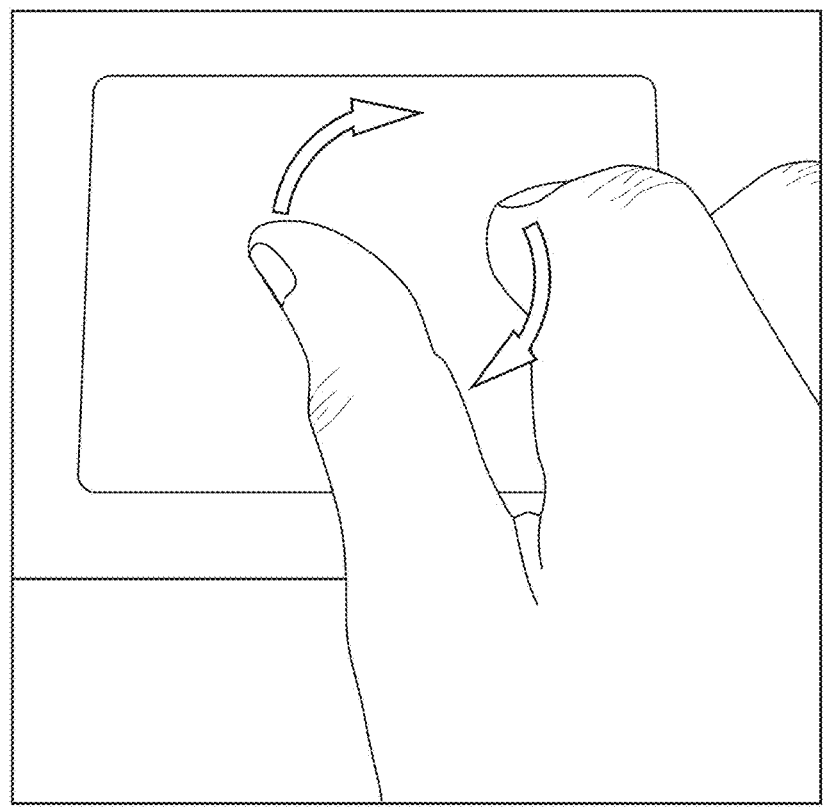
FIG. 26 illustrates a diagram of a swivel motion input at a user input device according to an illustrative embodiment.
Figure 27:
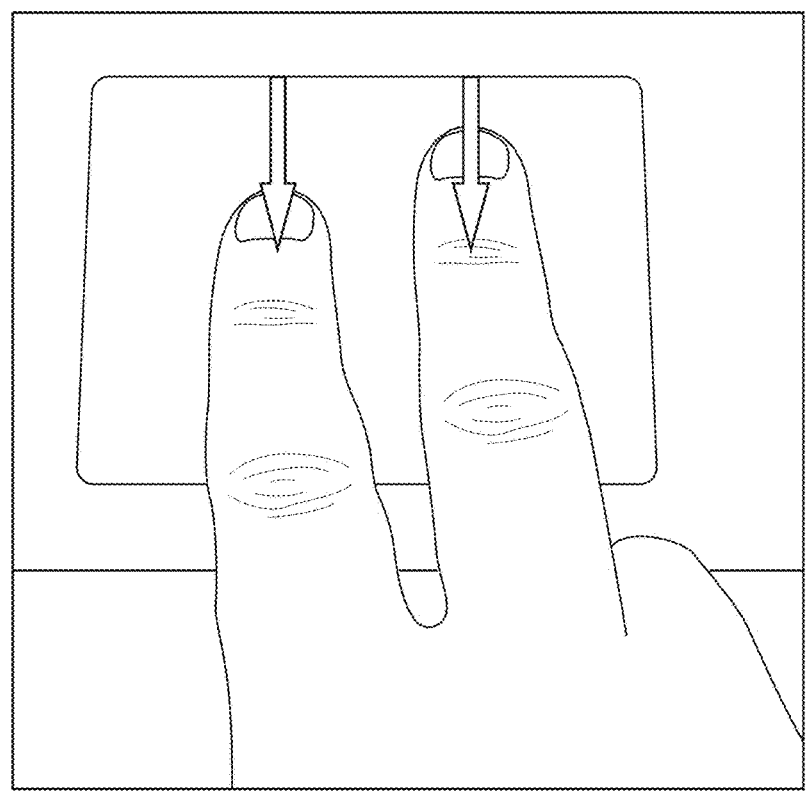
FIG. 27 illustrates a diagram of a tilt motion input at a user input device according to an illustrative embodiment.

Referring now to FIGS. 25-27, various examples of motions associated with controlling the position/orientation of display 20 are illustrated in accordance with various embodiments. The motions may be user input received at user input devices of ultrasound electronics module 26, such as user inputs received at touchscreens 110, 120. The user input may be provided using fingers or devices (e.g., touch devices, styluses, pens, etc.).

FIG. 25 illustrates an example of a user input indicating a command to shift the position of display 20 (e.g., a traverse command). Initial contact is made by two fingers, and the two fingers are shifted along the user input device in a substantially parallel direction. As shown in FIG. 25, the fingers are shifted along the user input device in a left-to-right manner (e.g., based on a frame of reference of a user facing display 20). This motion may indicate a command to traverse display 20 from left to right. Similarly, a right-to-left motion of the fingers could indicate a command to traverse display 20 from right to left.

FIG. 26 illustrates an example of a user input indicating a command to rotate display 20 about an axis substantially perpendicular to platform 22 (e.g., a swivel command). Initial contact is made by two fingers on the user input device, and the fingers are rotated on the user input device. As shown in FIG. 26, the fingers are rotated in a clockwise manner on the user input device (e.g., based on a frame of reference of a user facing the user input device). This motion may indicate a command to swivel display 20 clockwise. Similarly, a counterclockwise rotation of the fingers could indicate a command to swivel display 20 counterclockwise.

FIG. 27 illustrates an example of a user input indicating a command to tilt display 20 about an axis substantially parallel to a bottom edge (e.g., in a frame of reference of a user facing display 20) of display 20 (e.g., a tilt command). Initial contact is made by two fingers on the user input device, and the fingers are shifted down the user input device (e.g., away from display 20), which may indicate a command to tilt display 20 down towards ultrasound electronics module 26. Similarly, the fingers could be shifted up the user input device (e.g., towards display 20), indicating a command to tilt display 20 up.

In some embodiments, processing electronics of portable ultrasound system 100 are configured to identify a magnitude of the user input in order to generate motion commands having a corresponding magnitude. For example, processing circuit 404 as shown in FIG. 4 may be configured to identify a distance (e.g., absolute or relative distance) and/or rate of motion associated with the user input, and generate motion commands to transmit via display control module 428 having a corresponding magnitude. In other words, if processing circuit 404 identifies a relatively small distance of user input (such as moving fingers left to right a relatively small distance along the user input device), processing circuit 404 may generate a corresponding motion command configured to cause a relatively small motion of display 20. In some embodiments, processing circuit 404 and/or the user input device may be configured to identify a pressure of the input and modify movement of display 20 based on the pressure (e.g., such that greater pressure results in faster or more extensive movement and lower pressure results in slower or less extensive movement).

In some embodiments, various such motions may be received in combination, indicating commands indicating multiple desired motions of display 20. For example, any combination of traverse, tilt, and/or swivel commands may be received in combination, such as a motion in which fingers are shifted from left to right while rotated clockwise, indicating a command to traverse display 20 from left to right while also swiveling display 20 clockwise. Various processing electronics of portable ultrasound system 100 (e.g., processing circuit 404 shown in FIG. 4, etc.) may be configured to determine the commands indicated by such user inputs. Determining combined commands from user input may include associating portions of the user input with one or more of traverse, swivel, or tilt commands, identifying magnitudes associated with one or more of traverse, swivel, or tilt commands, identifying an order of one or more of traverse, swivel, or tilt commands, etc.

In some embodiments, a movable tool (e.g., mouse, joystick, etc.) can receive the user input. In some embodiments, the user input can be provided via a keyboard or other user input device.

Referring now to FIG. 28, display 20 includes one or more sensors configured to receive sensor input in accordance with one embodiment. As shown in FIG. 28, sensors 280 are positioned along a perimeter of display 20 adjacent to main screen 130. Sensors 280 may be a single continuous sensor, or discrete sensors. For example, discrete sensors 280 may be associated with receiving different user inputs corresponding to different commands. Sensors 280 may include pressure sensors, force sensors, capacitive sensors, resistive sensors, touch sensors, proximity sensors, etc.

In some embodiments, sensors 280 are configured to receive user input and output an indication of the user input, such as to a user input interface as illustrated in FIGS. 3-4. In response, electronics of portable ultrasound system 100 can be configured to set control of the position/orientation of display 20 into a neutral or manual mode. For example, in response to receiving an indication of the user input from sensors 280, processing electronics 402 can be configured to output a command to display control module 428 configured to cause display control module 428 to command display control actuator 432 to disengage drive mechanism 436 from display 20. In some embodiments, drive mechanism 436 is always in (or maintained in) engagement with display 20 unless a disengage command is received based on user input received at sensors 280.

In some embodiments, sensors 280 are configured to output the indication of the user input if the user input is received for a predetermined amount of time (e.g., half a second, one second, three seconds, etc.), such as to indicate that a user has grabbed display 20. In some embodiments, sensors 280 are configured to output a time associated with the user input along with the user input, and processing electronics 402 are configured to output a disengage command if the time is greater than a predetermined amount of time.

In some embodiments, sensors 280 are configured to receive user input indicating a command to cause one or more of a traverse, swivel, or tilt motion of display 20. Sensors 280 can be configured to detect a direction and/or magnitude of the user input, and output the direction and/or magnitude to processing electronics 402. Processing electronics 402 may be configured to determine if the user input indicates one or more of a traverse, tilt, or swivel command based on the user input including the direction and/or magnitude.

In some embodiments, sensors 280 may be positioned in discrete zones. For example, a first zone may be associated with receiving user input indicating a command to disengage drive mechanism 436 from display 20, a second zone may be associated with receiving user input indicating a traverse command, a third zone may be associated with receiving user input indicating a swivel command, and a fourth zone may be associated with receiving user input indicating a tilt command. Glass of display 20 may be marked (e.g., etched, etc.) to demarcate the discrete zones.

In some embodiments, display 20 and/or associated drive systems are also modular and can be replaced, upgraded, or otherwise modified. For example, ultrasound electronics module 26 and display 20 can be replaced with different components. In another example, ultrasound electronics module 26, display 20, and drive system 500 can each be replaced with an integrated portable electronic device. Portions of platform 22 may also be replaced. As such, portable ultrasound system 100 can be made modular to allow significant interchangeability of ultrasound components, such as by providing a base/supporting structure allowing a wide variety of ultrasound systems to be supported. In some embodiments, the base/supporting structure do not include any electronics. In some embodiments, the base/supporting structure include a backup battery or other power supply. In some embodiments, an entire top portion of portable ultrasound system 100 (e.g., including platform 22 and other support structures) can be removed, leaving only a base or only a base and a support structure. This may allow a variety of platforms to be attached to the base and/or support structure for supporting portable ultrasound systems. For example, in some embodiments, the portable ultrasound system 100 is designed such that a structure configured to receive modular ultrasound electronics modules and electronically coupled the modular ultrasound electronics modules to a display can be mounted in one configuration, and can be removed and replaced with a laptop or other device that includes both the ultrasound electronics modules and the display integrated within its housing(s). This may allow for the portable ultrasound system 100 to be used both with modules located at a facility having the portable ultrasound system 100 and by a user (e.g., physician, etc.) providing a remote ultrasound system such as a laptop or other standalone portable electronic device.

In some embodiments, sensors 280 can include eye tracking features. For example, sensors 280 can include a camera configured to track a position of a target, such as eyes of a user operating portable ultrasound system 100, or an instrument such as an ultrasound probe. Eye tracking sensors 280 may be located on various locations of portable ultrasound system 100 other than display 20, including ultrasound electronics module 26 and platform 22. Various processing electronics of portable ultrasound system 100, such as processing electronics 402, can receive and process tracking data from eye tracking sensors 280. For example, based on the tracking data, processing electronics 402 can generate commands configured to control drive mechanism 436 to control the position/orientation of display 20. In some embodiments, processing electronics 402 can thus traverse, tilt, and/or swivel display 20 to maintain (e.g., shorten, align, etc.) a line of sight for a user with display 20. In some embodiments, processing electronics 402 are configured to identify if the user is looking at display 20 with at least one eye, so as to distinguish between when a user desires to look at display 20 and look at a patient. In response to determining that the user desires to look at display 20, processing electronics 402 may be configured to generate control commands to position/orient display 20 to shorten or align a line of sight between display 280 and the user.

Figure 29:
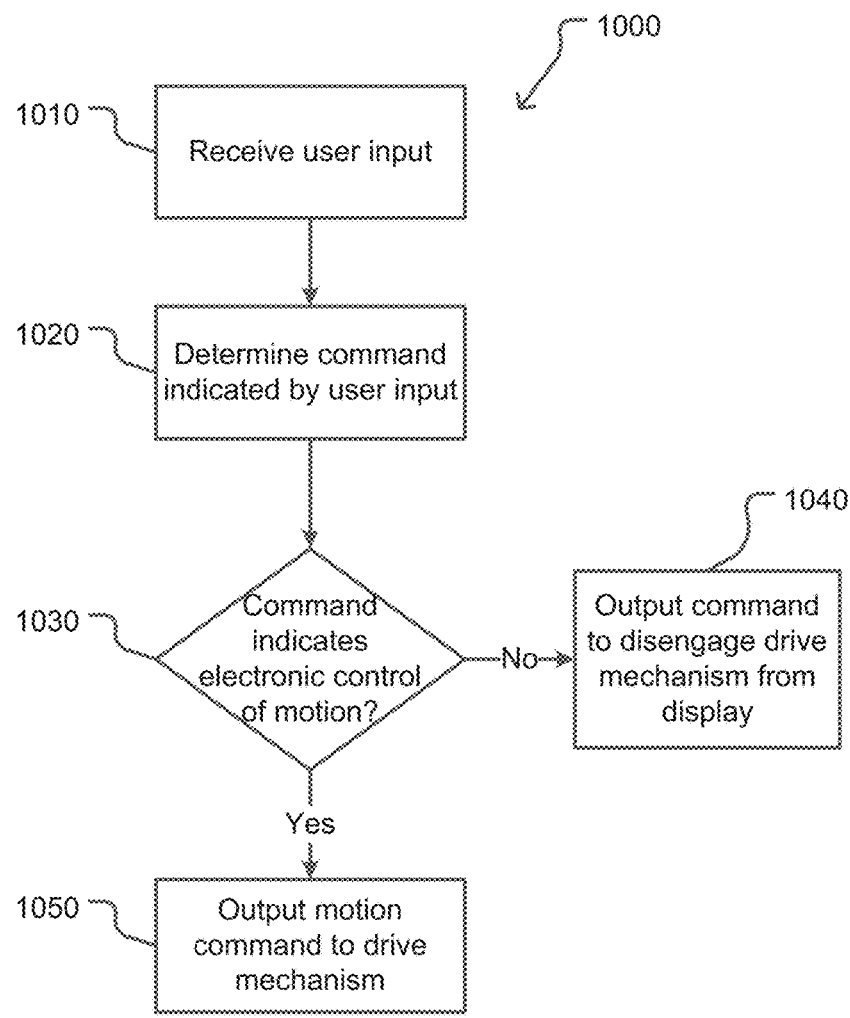
FIG. 29 illustrates a flow diagram of a method of controlling motion of a display of a portable ultrasound system according to an illustrative embodiment.

Referring now to FIG. 29, a method 1000 for controlling motion of a display of a portable ultrasound system is illustrated. The method 1000 can be performed using a variety of systems as described herein, including portable ultrasound system 100 and control system 400.

At 1010, user input is received at a user input device (e.g., touchscreens 110, 120; sensors 280). For example, user input may be received as a touch motion on touchscreens 110, 120; user input may be received as a touch, force, grasp, or other input at sensors 280.

At 1020, a command indicated by the user input is determined. For example, processing electronics 402 can receive the user input, and determine whether the user input indicates one or more of a traverse, swivel, or tilt command. The command indicated by the user input may be determined based on directions and/or magnitudes of the user input.

At 1030, a determination is made as to whether the command indicates electronic control of motion. In some embodiments, if the user input is received at a user input device of ultrasound electronics module 26 (e.g., at a touchscreen), then the command is determined to indicate electronic control of motion. In some embodiments, if the user input is received at a user input device of display 20 (e.g., at sensors), then the command is determined to not indicate electronic control of motion. In some embodiments, if the user input is received at a user input device of display 20 and the user input has certain characteristics (e.g., direction, magnitude, force, pressure, duration, etc.), then the command is determined to indicated electronic control of motion.

At 1040, in response to determining that the command does not indicate electronic control of motion, a command is outputted to disengage a drive mechanism (e.g., drive mechanism 436) from display 20. For example, an actuator may mechanically disengage drive mechanism 436 from display 20. This may allow a user to manually adjust the position/orientation of display 20 without resistance from drive mechanism 436.

At 1050, in response to determining that the command indicated by the user input does indicate electronic control of motion, a motion command is outputted to drive mechanism 436. For example, the command indicated by the user input can be a command to traverse display 20 from left to right, and a motion command configured to cause drive mechanism 436 to traverse display 20 from left to right is generated and outputted to drive mechanism 436.

Figure 30:
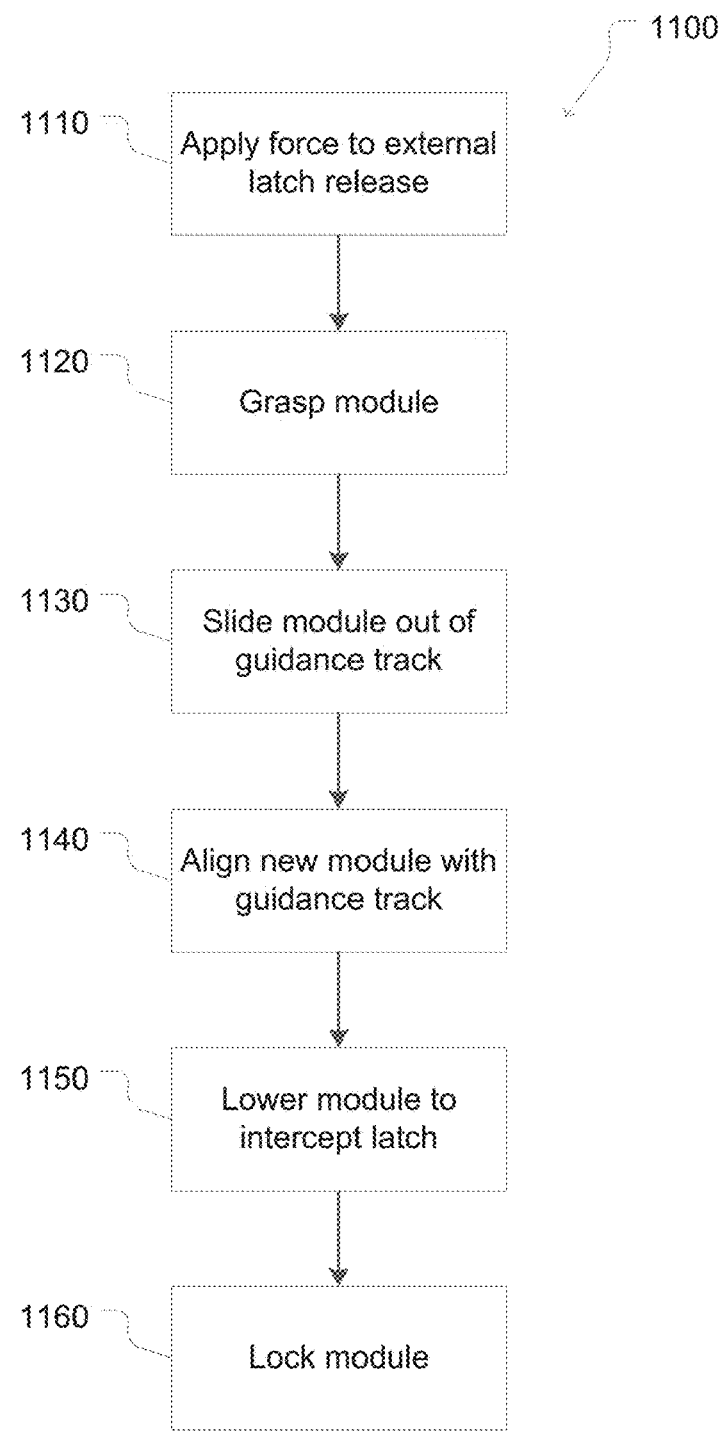
FIG. 30 illustrates a flow diagram of a method of replacing an ultrasound electronics module of a portable ultrasound system according to an illustrative embodiment.

Referring now to FIG. 30, a method 1100 of replacing a modular ultrasound electronics module is illustrated in accordance with one embodiment. The method 1100 can be performed using a variety of systems as described herein, including portable ultrasound system 100 and ultrasound electronics module 26. The method 1100 can be performed by a variety of users, including a user performing an ultrasound procedure.

At 1110, force is applied to an external latch release. In response, the external latch release releases a latch (e.g., a spring-loaded latch) that has snapped over a locking feature to hold the ultrasound electronics module in place. After the latch is released, the ultrasound electronics module rotates upward (e.g., away from platform 22, towards display 20, etc.).

At 1120, the ultrasound electronics module is grasped. For example, the ultrasound electronics module can include grasping features (e.g., handles, etc.) to be grasped by a user.

At 1130, the ultrasound electronics module is slid out of a guidance track. This allows the ultrasound electronics module to be electronically decoupled from any other electronic components and physically removed from the portable ultrasound cart system.

At 1140, a new ultrasound electronics module to be used with the portable ultrasound cart system is aligned with the guidance track. For example, the ultrasound electronics module can be positioned such that left and right edges of the ultrasound electronics module are aligned with left and right tracks.

At 1150, the ultrasound electronics module is lowered to intercept the latch (e.g., to engage a spring-loaded latch). At 1160, pressure is then applied to the ultrasound electronics module to lock the ultrasound electronics module into place. In this manner, the new ultrasound electronics module is modularly replaced into the portable ultrasound cart system, including being connected to any other electronic components.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. An ultrasound system, comprising:
   a display;
   an actuator configured to control at least one of a position or an orientation of the display;
   a user interface configured to receive a user input, the user input including a single gesture, the user input indicating at least one of a traverse command configured to cause the actuator to shift the display along a first axis, a swivel command configured to cause the actuator to rotate the display about a second axis, or a tilt command configured to cause the actuator to rotate the display about a third axis parallel to or collinear with the first axis; and
   a processing circuit configured to translate the single gesture into at least two of the traverse command, the swivel command, or the tilt command and cause the actuator to adjust the at least one of the position or orientation of the display based on the user input.

2. The ultrasound system of claim 1, wherein the display includes at least one sensor on a perimeter of the display, and the user interface is configured to receive the user input via the at least one sensor.

3. The ultrasound system of claim 1, wherein the display includes a display control circuit configured to transmit a control command to the actuator based on an output command received from the processing circuit, the display control circuit configured to store state information regarding the display and control the display based on the stored state information.

4. The ultrasound system of claim 3, wherein the state information includes a default position of the display, and the display control circuit is configured to cause the display to be placed in the default position in response to receive at least one of a reset command, an indication of a power up of the processing circuit, or an indication of a power down of the processing circuit.

5. The ultrasound system of claim 1, wherein the actuator is configured to deactivate electronic control of the display.

6. The ultrasound system of claim 1, wherein the processing circuit is configured to identify a first magnitude of the user input and cause the actuator to adjust the at least one of the position or orientation of the display by a second magnitude corresponding to the first magnitude.

7. An ultrasound system, comprising:
   a platform including a housing;
   a display attached to the housing;
   a drive system configured to adjust at least one of a position or an orientation of the display;
   at least one sensor attached to the display, the at least one sensor configured to receive an indication of a user input, the at least one sensor configured to detect a force and a direction associated with the user input; and
   a display control circuit configured to control operation of the drive system based on the indication of the user input by determining a movement for the display corresponding to the detected direction, comparing the force to a force threshold, and if the force is greater than the force threshold, causing the display to move according to the determined movement within a predetermined duration after the user input is received.

8. The ultrasound system of claim 7, wherein the at least one sensor includes a camera configured to track a position of a target, and generate the indication of the user input based on the tracked position of the target.

9. The ultrasound system of claim 7, wherein the at least one sensor includes:
   a first sensor positioned in a first zone, the first sensor configured to generate the indication to indicate a traverse command;
   a second sensor positioned in a second zone, the second sensor configured to generate the indication to indicate a swivel command; and
   a third sensor positioned in a third zone, the third sensor configured to generate the indication to indicate a tilt command.

10. The ultrasound system of claim 7, wherein the drive system includes:
    a tilt motor configured to rotate the display about a tilt axis parallel to and within a plane defined by the display;
    a traverse motor configured to translate the display along a traverse axis extending from a first side of the platform to a second side of the platform; and
    a swivel motor configured to rotate the display about a swivel axis perpendicular to the traverse axis.

11. The ultrasound system of claim 10, wherein the tilt motor, traverse motor, and swivel motor are located within the housing.

12. The ultrasound system of claim 10, wherein the display is configured to be located in a default position, and the drive system is configured to automatically align the display in the default position by translating the display to a center traverse position along the traverse axis, rotating the display to a center swivel position about the swivel axis, and subsequent to translating the display to the center swivel position and rotating the display to the center swivel position, rotating the display from a current tilt position to a tilt position corresponding to the default position.

13. The ultrasound system of claim 10, wherein the drive mechanism is configured to restrict motion of the display about the tilt axis when the display is outside of a center position along the traverse axis, and the ultrasound system includes a cam or ramp configured to align the display to a center swivel position about the swivel axis when the display is rotated to a default position.

14. A method, comprising:
   receiving, at a user interface, a user input indicating a command to control at least one of a position or an orientation of an ultrasound display;
   extracting the command from the user input; by a processing circuit; and
   controlling, by the processing circuit using a drive system in a second mode in which the drive system is engaged to the display, the at least one of the position or orientation of the ultrasound display based on the command responsive to the command indicating a second force received at the user interface greater than a second force threshold, the second force threshold greater than a first force threshold, wherein the display moves in response to receiving a first force greater than the first force threshold in a first mode of the drive system in which the drive system is disengaged from the ultrasound display.

15. The method of claim 14, further comprising storing, by a display control circuit, state information including a default position of the display, and causing the display to be placed in the default position in response to receiving at least one of a reset command, an indication of a power up of the processing circuit, or an indication of a power down of the processing circuit.

* * * * *